US008785343B2

(12) United States Patent
Liu et al.

(10) Patent No.: US 8,785,343 B2
(45) Date of Patent: Jul. 22, 2014

(54) MESOPOROUS CARBON SUPPORTED COPPER BASED CATALYST, PRODUCTION AND USE THEREOF

(75) Inventors: Jingwei Liu, Nanjing (CN); Zezhuang Li, Nanjing (CN); Shaohui Chen, Nanjing (CN); Aiwu Yang, Nanjing (CN); Jiye Bai, Nanjing (CN); Lijuan Liu, Nanjing (CN); Yingwu Wang, Nanjing (CN)

(73) Assignees: China Petroleum & Chemical Corp., Beijing (CN); Sinopec Yangzi Petrochemical Co., Ltd., Nanjing (CN)

( * ) Notice: Subject to any disclaimer, the term of this patent is extended or adjusted under 35 U.S.C. 154(b) by 0 days.

(21) Appl. No.: 13/595,260

(22) Filed: Aug. 27, 2012

(65) Prior Publication Data
US 2013/0131418 A1 May 23, 2013

(30) Foreign Application Priority Data
Nov. 21, 2011 (CN) .......................... 2011 1 0371388

(51) Int. Cl.
| | |
|---|---|
| *B01J 21/18* | (2006.01) |
| *B01J 23/00* | (2006.01) |
| *B01J 23/02* | (2006.01) |
| *B01J 23/04* | (2006.01) |
| *B01J 23/06* | (2006.01) |
| *B01J 23/08* | (2006.01) |
| *B01J 23/10* | (2006.01) |
| *B01J 23/20* | (2006.01) |
| *B01J 23/70* | (2006.01) |
| *B01J 23/72* | (2006.01) |
| *C01B 31/00* | (2006.01) |
| *C01B 31/02* | (2006.01) |
| *C07C 5/333* | (2006.01) |
| *D01F 9/12* | (2006.01) |

(52) U.S. Cl.
USPC ........... 502/182; 502/183; 502/184; 502/303; 502/304; 502/340; 502/341; 502/342; 502/343; 502/344; 502/345; 502/346; 502/349; 502/353; 502/354; 502/355; 423/445 R; 423/447.1; 423/447.2; 585/661

(58) Field of Classification Search
USPC .............. 502/182–184, 305–355; 423/445 R, 423/447.1, 447.2; 585/661
See application file for complete search history.

(56) References Cited

U.S. PATENT DOCUMENTS

| | | | | |
|---|---|---|---|---|
| 5,962,367 | A * | 10/1999 | Shen et al. | 502/439 |
| 6,417,135 | B1 * | 7/2002 | Dyroff | 502/325 |
| 7,811,959 | B2 * | 10/2010 | Lee et al. | 502/180 |
| 8,119,555 | B2 * | 2/2012 | Banerjee et al. | 502/174 |
| 2008/0177117 | A1 * | 7/2008 | Benderly et al. | 585/324 |

OTHER PUBLICATIONS

"Relationship between Pore Connectivity and Mean Pore Size in Modulated Mesoporous Vanado-Phosphoro-Aluminates and Some Similarites with the Branching of Trees," P. J. Pomonis et al. Langmuir 2001, 17, pp. 8397-8404.*
"Sustained Release of Heparin on Enlarged-Pore and Functionalized MCM-41," Mi Mi Wan et al. Applied Materials and Interfaces, 2012, 4, pp. 4113-4122.*
"Revisiting the Most Probable Pore-size Distribution in Filter Media:: The Gamma Distribution," Peter R. Johnston. Filtration & Separation, Apr. 1998, pp. 287-292.*
Hiroshi Shimada et al., "Dehydrogenation of isobutane to isobutane with iron-loaded activated carbon catalyst," Applied Catalysts A: General, vol. 168, pp. 243-250 (1998).
Jan Ogonowski et al., "Carbon dioxide in the dehydrogenation of isobutane over $VMgO_x$," Catalysts Communications, vol. 11, pp. 132-136 (2009).
Jian Fei Ding et al., "Coupling dehydration of isobutane in the presence of carbon dioxide over chromium oxide supported on active carbon," ScienceDirect, Chinese Chemical Letters, vol. 19, pp. 1059-1062 (2008).
Yu'an Huang et al., "Mesoporous carbon materials prepared from carbohydrates with a metal chloride template," J. Mater. Chem., vol. 19, pp. 7759-7764 (2009).
Jianfel Ding et al., Catalystic dehydrogenation of isobutane in the presence of carbon dioxide over nickel supported on active carbon, Journal of Molecular Catalysis A; Chemical, vol. 315. pp. 221-225 (2010).

* cited by examiner

*Primary Examiner* — Patricia L Hailey
(74) *Attorney, Agent, or Firm* — Finnegan, Henderson, Farabow, Garrett & Dunner LLP

(57) ABSTRACT

This invention relates to a mesoporous carbon supported copper based catalyst comprising mesoporous carbon, a copper component and an auxiliary element supported on said mesoporous carbon, production and use thereof. The catalyst is cheap in cost, friendly to the environment, and satisfactory in high temperature resistance to sintering, with a highly improved and a relatively stable catalytic activity.

17 Claims, No Drawings

MESOPOROUS CARBON SUPPORTED COPPER BASED CATALYST, PRODUCTION AND USE THEREOF

This application claims priority to the Chinese patent application No. 201110371388.2, filed on Nov. 21, 2011, the content of which is fully incorporated by reference herein.

TECHNICAL FIELD

This invention relates to a copper based catalyst, specifically to a mesoporous carbon supported copper based catalyst. This invention further relates to production of the mesoporous carbon supported copper based catalyst and use thereof in dehydrogenation of a $C_2$ to $C_{12}$ chain alkyl compound.

BACKGROUND ART

Dehydrogenating a less costly $C_2$ to $C_{12}$ chain alkyl compound (for example, ethane, butene, isobutane, ethyl benzene, ethyl cyclohexane, etc., also simply referred to as chain alkyl compound hereinafter) to the corresponding chain alkenyl compound, which is more valuable, has drawn more and more attention of the industry and the academia. For example, as a very important starting material for the organic chemical industry, isobutene among the $C_4$ olefins traditionally mainly originates from an apparatus for producing ethylene by a naphtha stream cracking process or an apparatus by heavy oil fluid catalytic cracking in a processing plant. As the modern chemical industry is growing demand for isobutene as a starting material, a process for producing isobutene from isobutane by a dehydrogenation process has been developed and has ranked the third as a source of isobutene in the world.

The prior art isobutane dehydrogenation process in an industry scale is generally conducted under an oxygen free condition, by using a Cr based catalyst or a Pt based catalyst. For example, the Catofin process of the ABB Lummus company, the Oleflex process of the UOP company, the Star process of the Philips company, the Linde process of the Linde company and the FBD-4 process of the Snamprogetti company can be exemplified.

These prior art processes suffer from such problems as, use of a Cr based catalyst which is toxic, or a Pt based catalyst which is expensive, which lead to cost or environment pollution concerns. Further, restricted by the thermodynamic equilibrium of the dehydrogenation reaction, these prior art processes give a relatively lower isobutane conversion level. It may be possible to increase this conversion by elevating the reaction temperature, however, a relatively high reaction temperature will generally lead to sintering, coke deposition and deactivation of the catalyst. For this reason, there still remains room for the prior art catalyst to improve its high temperature resistance.

The dehydrogenation under a $CO_2$ atmosphere has drawn more and more attention. Ogonowski et al compared the dehydrogenation activity for isobutane over a V—Mg—O catalyst having a surface area of 21 $m^2\ g^{-1}$ under a reaction temperature of 600° C., under an inert atmosphere (He), with that under a $CO_2$ atmosphere. The result reveals that the catalyst exhibits an improved dehydrogenation activity under the $CO_2$ atmosphere, resulting in an isobutane conversion as high as 13% and an isobutene selectivity of more than 80% (Catalysis Communications, Vol. 11, 2009, pp. 132-136). Shimada et al found that the isobutane conversion can reach at as high as 23% under 600° C. by using an activated carbon supported $Fe_2O_3$ catalyst, with an isobutene selectivity of 80%. Unfortunately, the activity of the catalyst decays very rapidly, reflected by an isobutane conversion reduced to 13% after 3 hours (Applied Catalysis A: General, Vol. 168, 1998, pp. 243-250). Ding et al found that both an activated carbon supported $Cr_2O_3$ catalyst and an activated carbon supported NiO catalyst exhibit a relatively high initial activity for isobutane dehydrogenation in a $CO_2$ atmosphere, while both suffer from a relatively rapid activity decay (Chinese Chemical Letters, Vol. 19, 2008, pp. 1059-1062; Journal of Molecular Catalysis A: Chemical, Vol. 315, 2010, pp. 221-225).

Nevertheless, these prior art catalysts are incapable of concretely meet with some requirements in practice due to their insufficient isobutane conversion and isobutene selectivity, and there still remains room for further improvement in this regard. Further, the rapid activity decay is also a hard problem to be solved.

The prior art catalysts suffer from the similar defects when used for dehydrogenating other $C_2$ to $C_{12}$ chain alkyl compounds than isobutane.

Under this circumstance, there still need a catalyst in this field, especially a catalyst for dehydrogenating a $C_2$ to $C_{12}$ chain alkyl compound, which is cheap in cost, friendly to the environment, and satisfactory in high temperature resistance to sintering, with a highly improved and a relatively stable catalytic activity, and capable of solving the problems associated with the prior art catalysts.

SUMMARY OF THE INVENTION

On the basis of the prior art, the present inventors found that by using copper as the main metal active component, and further supporting same onto a mesoporous carbon, in combination with a suitable auxiliary element as needed, the problems identified as aforesaid can be successfully solved, whereby coming at the present invention.

Specifically, the present invention involves the following aspects.

1. A mesoporous carbon supported copper based catalyst, characterized by a composition comprising mesoporous carbon, a copper component and an auxiliary element supported on said mesoporous carbon, wherein, the auxiliary element (expressed as oxide) is one or more selected from the group consisting of $V_2O_5$, $Li_2O$, MgO, CaO, $Ga_2O_3$, ZnO, $Al_2O_3$, $CeO_2$, $La_2O_3$, $SnO_2$ and $K_2O$, preferably $SnO_2$, $Li_2O$, a combination of $SnO_2$ and $Li_2O$, a combination of $SnO_2$ and $K_2O$, a combination of $Li_2O$ and $K_2O$, or a combination of $SnO_2$, $K_2O$ and $Li_2O$, based on the total weight of the catalyst, the amount of the copper component (calculated as CuO) is 2-20 wt %, preferably 3-15 wt %, based on the total weight of the catalyst, the amount of the auxiliary element (calculated as the aforesaid oxide) is 0-3.0 wt %, preferably 0-2.9 wt %, more preferably 0.2-2.0 wt %, and based on the total weight of the catalyst, the amount of the mesoporous carbon is 77.1-98 wt %, preferably 83-96.8 wt %, more preferably the remaining.

2. The mesoporous carbon supported copper based catalyst according to any of the aforesaid aspects, wherein the catalyst is substantially consisted of the mesoporous carbon, the copper component and the auxiliary element.

3. The mesoporous carbon supported copper based catalyst according to any of the aforesaid aspects, wherein the mesoporous carbon has a BET specific surface area of 900-3100 $m^2\ g^{-1}$, preferably 1200-3100 $m^2\ g^{-1}$, a most probable pore size of 2-8 nm, a pore volume of 0.4-3.2 mlg$^{-1}$, preferably 1.0-2.1 mlg$^{-1}$, a mesoporosity of 50-100%, preferably 75-100%.

4. The mesoporous carbon supported copper based catalyst according to any of the aforesaid aspects, wherein the mesoporous carbon is one or more selected from the group consisting of a mesoporous carbon having an ordered pore structure, a carbon nano-tube, a carbon nano-rod or a mesoporous carbon having a disordered pore structure.

5. A process for producing a mesoporous carbon supported copper based catalyst, characterized by comprising:

(1) a step of contacting a copper component precursor (such as a soluble salt of copper, such as a water soluble salt of copper, such as one or more selected from the group consisting of copper acetates, copper sulfates, copper nitrates and copper halides, such as one or more selected from the group consisting of copper acetates, copper nitrates and copper chlorides), an auxiliary element precursor (such as a soluble salt of the auxiliary element, such as a water soluble salt of the auxiliary element, such as one or more selected from the group consisting of acetates, sulfates, nitrates and halides of the auxiliary element, such as one or more selected from the group consisting of sulfates, nitrates and chlorides of the auxiliary element) and mesoporous carbon at a predetermined ratio, to obtain an intermediate product, and (2) a step of calcining the intermediate product to obtain the mesoporous carbon supported copper based catalyst, wherein, the auxiliary element (expressed as oxide) is one or more selected from the group consisting of $V_2O_5$, $Li_2O$, MgO, CaO, $Ga_2O_3$, ZnO, $Al_2O_3$, $CeO_2$, $La_2O_3$, $SnO_2$ and $K_2O$, preferably $SnO_2$, $Li_2O$, a combination of $SnO_2$ and $Li_2O$, a combination of $SnO_2$ and $K_2O$, a combination of $Li_2O$ and $K_2O$, or a combination of $SnO_2$, $K_2O$ and $Li_2O$, the predetermined ratio is such that the mesoporous carbon supported copper based catalyst resulted from the calcination has a composition as specified below, based on the total weight of the catalyst, the amount of the copper component (calculated as CuO) is 2-20 wt %, preferably 3-15 wt %, based on the total weight of the catalyst, the amount of the auxiliary element (calculated as the aforesaid oxide) is 0-3.0 wt %, preferably 0-2.9 wt %, more preferably 0.2-2.0 wt %, and based on the total weight of the catalyst, the amount of the mesoporous carbon is 77.1-98 wt %, preferably 83-96.8 wt %, more preferably the remaining.

6. The process according to any of the aforesaid aspects, wherein the contacting is conducted in the presence of a metal complexing agent, and the ratio by weight of the metal complexing agent to the copper component precursor is in the range of from 0.4 to 2.0.

7. The process according to any of the aforesaid aspects, wherein the calcination is conducted under a substantially oxygen free inert gas atmosphere at 500 to 750° C. (preferably 560-690° C.).

8. Use of the mesoporous carbon supported copper based catalyst according to any of the aforesaid aspects or use of a mesoporous carbon supported copper based catalyst produced by the process according to any of the aforesaid aspects in catalytic dehydrogenation of a $C_2$ to $C_{12}$ chain alkyl compound, to convert the $C_2$ to $C_{12}$ chain alkyl group on the compound into its corresponding chain alkenyl group.

9. Use according to any of the aforesaid aspects, wherein the $C_2$ to $C_{12}$ chain alkyl compound is isobutane, and the use comprises a step of contacting the mesoporous carbon supported copper based catalyst with a mixture feed of isobutane with $CO_2$, to convert isobutane into isobutene by a catalytic dehydrogenation reaction.

10. Use according to any of the aforesaid aspects, wherein the catalytic dehydrogenation reaction conditions include: a reaction temperature of 550-650° C., preferably 560-610° C., a reaction pressure of 0.05-1.0 MPa, preferably 0.06-0.5 MPa, a space velocity of 0.5-8 $Lg^{-1cat}h^{-1}$, ratio by molar of isobutane to $CO_2$ is 1:0.5 to 1:11.

EFFECT OF THE INVENTION

According to the present mesoporous carbon supported copper based catalyst, the process for producing same is relatively simply and feasible, eliminating the need of using an expensive or a toxic metal component during production, and the catalyst is thus rendered cheap in cost and environment friendly.

As compared with a prior art catalyst, by using the present mesoporous carbon supported copper based catalyst, a significantly improved conversion of the chain alkyl compound and selectivity to the corresponding chain alkenyl compound (for example, the conversion of the chain alkyl compound, for example isobutane, can be as high as 35-70%, preferably 50-75% or more, the selectively to the corresponding chain alkenyl compound, for example isobutene, can be as high as 70-98%, preferably 85-98%) can be obtained, with an additional merit that the activity of the catalyst remains stable over a relatively long period, indicating a slow activity decay. Due to this good performance in activity, it is possible to significantly reduce the reaction temperature involved in producing the corresponding chain alkenyl compound from an chain alkyl compound, if the present mesoporous carbon supported copper based catalyst has been used, which leads to significantly reduced production cost and energy consumption.

Further, compared with a prior art catalyst, the present mesoporous carbon supported copper based catalyst which exhibits a good high temperature resistance to sintering, even under a relatively elevated reaction temperature, is substantially free of the catalyst sintering, coke deposition, and deactivation concerns, which may facilitate further improvement in conversion of the chain alkyl compound (and that in the selectively to the chain alkenyl compound).

EMBODIMENT OF THE INVENTION

The invention is described more fully hereinafter with reference to specific embodiments. This invention may, however, be embodied in many different forms and should not be construed as limited to the embodiments set forth herein.

In the context of this invention, the term "chain alkyl", "chain alkane", "chain alkenyl" or "chain alkene" or the like refers to a straight chain or a branched chain (non-cyclic) alkyl, alkane, alkenyl or alkene respectively.

According to this invention, the terms "conversion" and "selectivity" refer to the single pass conversion of the $C_2$ to $C_{12}$ chain alkyl compound and the single pass selectivity to the corresponding chain alkenyl compound, respectively, i.e. the conversion or selectivity measured after contacting a fresh catalyst with a fresh feed of a $C_2$ to $C_{12}$ chain alkyl compound (or a fresh feed of a $C_2$ to $C_{12}$ chain alkyl compound with $CO_2$ in mixture) in a single pass to conduct a dehydrogenation reaction, not a cumulated conversion or selectivity measured after repeatedly contacting a recycled feed with said catalyst to conduct a dehydrogenation reaction.

According to this invention, provided is a mesoporous carbon supported copper based catalyst, whose composition comprises mesoporous carbon, a copper component (represented by CuO) and an auxiliary element (represented by its corresponding oxide) supported on said mesoporous carbon.

According to this invention, the copper component presents on the mesoporous carbon mainly in the form of a copper oxide. For example, calculated as Cu, the copper in the form of oxide (copper oxide) accounts for 50 wt % or more, such as 80 wt % or more, such as 90 wt % or more, of the total copper by weight on the mesoporous carbon. The copper oxide could be any stable oxide form of copper, for example CuO or its corresponding non-stoichiometric oxide, $Cu_xO_{1-x}$, wherein $0<x<1$, such as CuO. Nevertheless, for the convenience of representation and calculation, the copper component is expressed as CuO.

According to this invention, based on the total weight of the catalyst, the amount of the copper component (calculated as CuO) could be 2-20 wt %, such as 3-15 wt %.

Generally, according to this invention, the auxiliary element (expressed as its oxide) is one or more selected from the group consisting of $V_2O_5$, $Li_2O$, MgO, CaO, $Ga_2O_3$, ZnO, $Al_2O_3$, $CeO_2$, $La_2O_3$, $SnO_2$ and $K_2O$. In this case, based on the total weight of the catalyst, the amount of the auxiliary element (calculated as the aforesaid oxide) could be 0-3.0 wt %, such as 0-2.9 wt %, such as 0.2-2.0 wt %.

Specifically, according to this invention, the auxiliary element (expressed as its oxide) is one or more selected from the following groups A and B, Group A: $V_2O_5$, $Li_2O$, MgO, CaO, $Ga_2O_3$, ZnO, $Al_2O_3$, $CeO_2$, $La_2O_3$, and $SnO_2$, and Group B: $K_2O$.

In this case, according to this invention, based on the total weight of the catalyst, when selected from the Group A, the amount of the auxiliary element (calculated as the aforesaid oxide) could be 0-3.0 wt %, such as 0-2.9 wt %, such as 0.001-2.9 wt %, such as 0.2-2.0 wt %. Further, based on the total weight of the catalyst, when selected from the Group B, the amount of the auxiliary element (calculated as the aforesaid oxide) could be 0-3.0 wt %, such as 0-2.9 wt %, such as 0.001-2.9 wt %, such as 0.2-2.0 wt %, wherein a specific value of 1.2 wt % or any value that can be rounded up or down to 1.2 wt % could be excluded from each of these ranges. Or alternatively, according to this invention, based on the total weight of the catalyst, when selected from the Group B, the amount of the auxiliary element (calculated as the aforesaid oxide) could be 0.001-1.1 wt % or 1.3-2.9 wt %.

According to this invention, the auxiliary element presents on the mesoporous carbon mainly in the form of an auxiliary element oxide. For example, calculated as the auxiliary element, the auxiliary element in the form of oxide (auxiliary element oxide) accounts for 50 wt % or more, such as 80 wt % or more, such as 90 wt % or more, of the total auxiliary element by weight on the mesoporous carbon. The auxiliary element oxide could be any stable oxide form of said auxiliary element, for example the oxide represented by any of the aforesaid chemical formulae or its corresponding non-stoichiometric oxide, for example $Sn_yO_{2-y}$, wherein $0<y<2$, preferably the oxide represented by any of the aforesaid chemical formulae. Nevertheless, for the convenience of representation and calculation, the auxiliary element is expressed as the corresponding oxide as aforesaid.

According to this invention, these auxiliary elements can be used with one kind or with a combination of two or more kinds. In the case of use with a combination, the ratio by molar between any two auxiliary elements in the combination could be, but not limiting to, 1:10 to 10:1. According to this invention, preference is given to $SnO_2$, $Li_2O$, a combination of $SnO_2$ and $Li_2O$, a combination of $SnO_2$ and $K_2O$, a combination of $Li_2O$ and $K_2O$, or a combination of $SnO_2$, $K_2O$ and $Li_2O$.

According to this invention, when only one single auxiliary element is used, the aforesaid amount refers to the amount of said one single auxiliary element, while when a combination of two or more of the auxiliary elements is used as aforesaid, the aforesaid amount refers to the amount of these auxiliary elements in total.

According to this invention, with the further help of the auxiliary element, the activity decay problem associated with the prior art catalyst can be more effectively solved, whereby the catalyst produced according to this invention is characterized by a stable catalytic activity over a relatively long period. For example, when the catalyst according to this invention is used for producing the corresponding chain alkenyl compound by dehydrogenation reaction from a chain alkyl compound, as compared with the activity (expressed by the conversion of the chain alkyl compound, for example, isobutane) measured at 1 hour after the beginning of the reaction, the activity measured at 3 hour after the beginning of the reaction drops at most by 20%, preferable at most by 15%, such as at most by 10% or 5% or 2%. Further, the selectivity over the catalyst to the chain alkenyl compound remains nearly constant throughout the reaction (for example, over a reaction time of 3 hours or more), with a variation of ±2% or less, preferably ±1% or less, if any.

According to this invention, based on the total weight of the catalyst, the amount of the mesoporous carbon could be 77.1-98 wt %, such as 83-96.8 wt %, or the remaining of the catalyst.

According to this invention, when the amount of the mesoporous carbon presents as the remaining, based on the total weight of the catalyst, the catalyst according to this invention is substantially consisted of the mesoporous carbon, the copper component and the auxiliary element. By "substantially", it means that the catalyst herein could further contain any impurities inevitably introduced or any by-products inevitably generated during production of the catalyst, in addition to the mesoporous carbon, the copper component and the auxiliary element. Generally, the amount of these impurities or by-products is so little (as low as 1 wt % or less) that they do not substantially or significantly interfere with the catalyst's bringing its activity into full play.

According to an embodiment of this invention, the mesoporous carbon supported copper based catalyst of this invention contains no element which is expensive (for example, Pd, Pt, Au, Ag, Rh, Ir, Ru etc.) or is toxic or triggers environmental concerns (for example, Cr, Pb, Cd, As, Hg, Os etc.), thereby is characterized by a low cost and an environmental friendly nature.

According to this invention, the mesoporous carbon has a BET specific surface area of 900-3100 $m^2 g^{-1}$, preferably 1200-3100 $m^2 g^{-1}$, a most probable pore size of 2-8 nm, a pore volume of 0.4-3.2 $mlg^{-1}$, preferably 1.0-2.1 $mlg^{-1}$, a mesoporosity of 50-100%, preferably 75-100%.

According to this invention, the mesoporous carbon is one or more selected from the group consisting of a mesoporous carbon having an ordered pore structure, a carbon nano-tube, a carbon nano-rod or a mesoporous carbon having a disordered pore structure (for example, a disordered mesoporous carbon produced by carbonization of an organic carbohydrate compound or metal halide).

The mesoporous carbon could be commercial available (for example, a trade name of CMK-1 or CMK-3, as a commercial available mesoporous carbon having an ordered pore structure), or could be produced by a known process (for example, reference can be made to Journal of Materials Chemistry, Vol. 19, 2009, pp. 7759-7764).

According to this invention, there is no special limitation as to the particle size of the mesoporous carbon, as long as it meets with the requirements as set for a carrier in a catalyst. For example, the particle size could be, but not limiting to, 10 to 10000 nm, or 10 to 1000 nm, or 10 to 100 nm. When the mesoporous carbon is of a non-spherical shape, the particle size refers to the size of long axis or length, which is obvious to a person skilled in the art.

According to this invention, if not confined by any theory, it is believed that by using the mesoporous carbon as the carrier, the thus produced catalyst will be provided with a relatively higher specific surface area and greater pore size, which facilitates rapid diffusion of the reactants and products through the pore channel. As compared with a prior art catalyst (for example, a normal activated carbon supported catalyst), the present mesoporous carbon supported copper based catalyst exhibits a relatively improved high temperature resistance, and even under a relatively elevated reaction temperature, is substantially free of catalyst sintering, coke deposition, and deactivation concerns, which may facilitate further improvement in conversion of the chain alkyl compound (and that in the selectively to the chain alkenyl compound).

According to this invention, further provided is a process for producing the mesoporous carbon supported copper based catalyst, characterized by comprising:

(1) a step of contacting a copper component precursor, an auxiliary element precursor and mesoporous carbon at a predetermined ratio (preferably in the presence of a dispersing media for example water), to obtain an intermediate product (referred to as contacting step hereinafter), and (2) a step of calcining the intermediate product to obtain the mesoporous carbon supported copper based catalyst (referred to as calcination step hereinafter).

According to this invention, the predetermined ratio is such that the mesoporous carbon supported copper based catalyst resulted from the calcination step has a composition as aforesaid specified.

According to this invention, the term "copper component precursor" refers to a compound capable of generating the aforesaid copper oxide (for example CuO) after calcinated in the calcination step (2). Preference is given to a soluble salt of copper, such as a water soluble salt of copper, such as one or more selected from the group consisting of copper acetates, copper sulfates, copper nitrates and copper halides, such as one or more selected from the group consisting of copper acetates, copper nitrates and copper chlorides, such as copper (II) acetate, copper (II) nitrate or copper (II) chloride etc.

According to this invention, the copper component precursor can be used with one kind or with a combination of two or more kinds.

According to this invention, the term "auxiliary element precursor" refers to a compound capable of generating the aforesaid auxiliary element oxide (for example, that represented by the aforesaid chemical formulae) after calcinated in the calcination step (2). Preference is given to a soluble salt of the auxiliary element, such as a water soluble salt of the auxiliary element, such as one or more selected from the group consisting of acetates, sulfates, nitrates and halides of the auxiliary element, such as one or more selected from the group consisting of sulfates, nitrates and chlorides of the auxiliary element, such as $SnCl_4$, $SnSO_4$, $LiNO_3$, $KNO_3$, $CH_3COOLi$ or $CH_3COOK$, etc.

According to this invention, the auxiliary element precursor can be used with one kind or with a combination of two or more kinds.

According to this invention, there is no specific limitation as to the sequence or order in which the respective starting components (i.e. the copper component precursor, the auxiliary element precursor and the mesoporous carbon) contact with each other in the contacting step. Further, according to this invention, there is no specific limitation as to how to conduct the contacting step, as long as the respective starting components contact with each other so sufficiently that a homogeneous intermediate product can be obtained. For example, it is acceptable to mix the respective starting components till homogeneous by any means known in this field (if needed, with stirring).

If needed, in order for a more sufficient and homogeneous contacting, or for the convenience of contacting, the contacting step could be conducted in the presence of a dispersing media for example, water. The intermediate product thus obtained could be in the form of slurry.

The contacting step could be conducted at any temperature in the range of from 0 to 90° C., such as from the ambient temperature to about 80° C., but not limiting thereto. The contacting step could be conducted for such a duration that a homogeneous intermediate product can be effectively obtained, generally but not limiting to, 0.05 to 5 hours.

According to this invention, after the intermediate product is produced, especially in the form of slurry, it is acceptable to dry same by any means known in this field (for example, at 60-150° C., or 70-120° C.), to remove any dispersing media (for example water) that may have been introduced during the production. According to this invention, the thus dried intermediate product is also simply referred to as intermediate product.

According to this invention, the contacting step could be conducted in the presence of a metal complexing agent (preferably a water soluble metal complexing agent), a stabilizing agent and a pH adjusting agent, etc.

According to this invention, the ratio by weight of the metal complexing agent to the copper component precursor could be 0.4 to 2.0. The metal complexing agent helps to improve the dispersion of the active components (i.e. the copper component and the auxiliary element) on the mesoporous carbon and contributes to improvement of the activity of the catalyst.

As the metal complexing agent, exemplified is a polybasic carboxylic acid, a polybasic alcohol and a polyamine, etc. The metal complexing agent can be used with one kind or with a combination of two or more kinds. In the case of use with a combination, the ratio by weight of the metal complexing agents in total to the copper component precursor is in the range of 0.4 to 2.0.

As the polybasic carboxylic acid, exemplified is a $C_{2-20}$ alkane carrying 2 to 10 (preferably 3 to 6) carboxyl groups, for example, oxalic acid, succinic acid, etc. As the polybasic carboxylic acid, further exemplified is a $C_{2-20}$ alkane carrying one or more (for example, 1 to 6) hydroxyl group(s), and at the same time, 2 to 10 (preferably 3 to 6) carboxyl groups, for example, malic acid, tartaric acid, citric acid, etc. Or else, as the polybasic carboxylic acid, further exemplified is a poly carboxylalkyl (poly)amine obtained by interrupting the aforesaid $C_{2-20}$ alkane chain with one or more nitrogen atom (s), for example, nitrilotriacetic acid, EDTA, etc.

As the polybasic alcohol, exemplified is a $C_{2-20}$ alkane carrying 2 to 10 (preferably 3 to 6) hydroxyl groups, for example, ethylene glycol, or a polymer of said polybasic alcohol, for example, polyethylene glycol, or a poly hydroxylalkyl (poly)amine obtained by interrupting the aforesaid $C_{2-20}$ alkane chain with one or more nitrogen atom(s), for example, monoethanol amine, triethanol amine, etc.

As the polyamine, exemplified is ethylene diamine, bisethylene triamine, triethylene tetramine, etc.

As the stabilizing agent, exemplified is that known in this field, for example, ammonium chloride, ammonium sulfate, etc. As the pH adjusting agent, exemplified is hydrochloric acid, ammonia, etc.

According to this invention, the metal complexing agent (and further the stabilizing agent and the pH adjusting agent, both of which are optionally used as needed) could be introduced into the contacting step to contact with the mesoporous carbon, together with or before or after introduction of the copper component precursor and/or the auxiliary element precursor, without any specific limitation thereto.

According to this invention, the copper component precursor and/or the auxiliary element precursor and/or the metal complexing agent could be used in the form of solution. For the convenience of operation, an aqueous solution is preferred. To this end, the copper component precursor, the auxiliary element precursor and the metal complexing agent could be dissolved into a solution separately, and then the respective solutions could be introduced into the contacting step simultaneously or one after another, or be dissolved as a mixture solution of two or three, and then the mixture solution could be introduced into the contacting step, without any specific limitation thereto. Together with or after this introduction, the aforesaid stabilizing agent, pH adjusting agent, etc. could be further introduced as needed by any means known in this field at a commonly known amount.

According to an embodiment of this invention, the contacting step comprises:

(1a) A step of metering and mixing together and dissolving in water a predetermined amount of the copper component precursor, the auxiliary element precursor and the metal complexing agent, wherein the ratio by weight of the metal complexing agent to the copper component precursor is in the rang of from 0.4 to 2.0, optionally, to which a suitable amount of the stabilizing agent, the pH adjusting agent and etc. is further added if needed, to obtain an aqueous solution, (1b) A step of mixing the aqueous solution with a predetermined amount of mesoporous carbon with stirring, to obtain a slurry, and (1c) A step of drying the slurry (for example, at 60 to 150° C., or 70 to 120° C.), to obtain the intermediate product.

According to this invention, the "predetermined amount" prescribed herein for the copper component precursor, the auxiliary element precursor and the mesoporous carbon is such that the mesoporous carbon supported copper based catalyst resulted from the calcination step has a composition meeting with the requirements as herein aforesaid specified, with no more further specific limitation thereto. In view of this, a person skilled in the art may determine a suitable "predetermined amount" for each starting component by referring to these requirements without any further specific limitation.

According to this invention, the resultant intermediate product is calcined in the calcination step as follows, so as to obtain the mesoporous carbon supported copper based catalyst of this invention. By this calcination, 50 wt % or more, such as 80 wt % or more, such as 90 wt % or more, of the total copper (calculated as Cu) contained in the copper component precursor supported on the mesoporous carbon could be converted into the aforesaid copper oxide, and 50 wt % or more, such as 80 wt % or more, such as 90 wt % or more, of the total auxiliary element (calculated as the auxiliary element) contained in the auxiliary element precursor supported on the mesoporous carbon could be converted into the aforesaid corresponding auxiliary element oxide.

According to this invention, the content of the copper component and that of the auxiliary element in the thus obtained mesoporous carbon supported copper based catalyst could be determined by a conventional element analysis technology, for example the ICP (Inductively Coupled Plasma) or the XRF (X-ray Fluorescence Analysis), etc, expressed as the corresponding oxide as aforesaid.

The calcination step could be conducted under a substantially oxygen free inert gas atmosphere at 500 to 750° C. (preferably 560-690° C.). The calcination could be conducted for a duration of generally 3 to 8 hours, but not limiting thereto. By "a substantially oxygen free inert gas atmosphere", it refers to a high purity $N_2$ gas atmosphere, a high purity Ar gas atmosphere or a high purity He gas atmosphere, whose $O_2$ concentration remains constantly less than 0.1% by volume.

According to this invention, further related to is use of the aforesaid mesoporous carbon supported copper based catalyst of this invention or use of a mesoporous carbon supported copper based catalyst produced by the aforesaid process of this invention in catalytic dehydrogenation of a $C_2$ to $C_{12}$ chain alkyl compound, to convert the $C_2$ to $C_{12}$ chain alkyl group on the compound into its corresponding chain alkenyl group.

As the $C_2$ to $C_{12}$ chain alkyl compound, exemplified is any compound carrying one or more $C_2$ to $C_{12}$ chain alkyl group(s), for example, an organic skeleton (for example, ethers, hydrocarbons, esters, heterocyclic compounds, silicones, silanes, polymers, celluloses, etc.) or an inorganic skeleton (for example, titanate esters, silicate esters, silicon atom, magnesium atom, aluminum atom, etc.) carrying one or more $C_2$ to $C_{12}$ chain alkyl group(s). Preference is given to a $C_{0-30}$ hydrocarbon carrying one or more $C_2$ to $C_{12}$ chain alkyl group (s).

As the $C_{0-30}$ hydrocarbon, exemplified is a $C_{1-30}$ chain alkane for example, methane, ethane, propane and etc, a $C_{3-30}$ cyclic alkane for example, cyclic propane, cyclic butane, cyclic hexane, and etc, a $C_{2-30}$ chain alkene for example ethene, propene, and etc, a $C_{4-30}$ cyclic alkene for example, cyclic butene, cyclic hexene, and etc, a $C_{2-30}$ alkyne for example, ethyne, propyne, and etc, and a $C_{6-30}$ aromatic hydrocarbon for example benzene, toluene, ethyl benzene, naphthalene, styrene and etc.

According to this invention, in the case of $C_0$ hydrocarbon, i.e. the expression "$C_0$ hydrocarbon carrying one or more $C_2$ to $C_{12}$ chain alkyl group(s)" refers to the $C_2$ to $C_{12}$ chain alkane, for example, a $C_2$ to $C_6$ chain alkane, for example, ethane, propane, n-butane, isobutane, tertiary butane, n-pentane, iso-pentane, n-hexane, and etc.

According to this invention, it is obvious that each of said one or more $C_2$ to $C_{12}$ chain alkyl group(s) presents in the $C_2$ to $C_{12}$ chain alkyl compound as a pendant group on the skeleton of the compound.

According to this invention, it is preferable for the $C_2$ to $C_{12}$ chain alkyl compound to carry 1 to 5 (preferably 1 to 3, or 1 or 2) of the $C_2$ to $C_{12}$ chain alkyl group(s). As the $C_2$ to $C_{12}$ chain alkyl group, exemplified is ethyl, n-propyl, iso-propyl, n-butyl, iso-butyl, sec-butyl, n-pentyl, etc, wherein preference is given to a $C_2$ to $C_6$ chain alkyl group, for example ethyl.

According to this invention, as the $C_{0-30}$ hydrocarbon carrying one or more $C_2$ to $C_{12}$ chain alkyl group(s), preference is given to a $C_{0-30}$ hydrocarbon carrying one ethyl, for example, ethane, propane, isobutane, iso-pentane, ethyl benzene, ethyl cyclohexane, and etc.

The $C_2$ to $C_{12}$ chain alkyl compound can be used with one kind or with a combination of two or more kinds.

According to this use of this invention, the mesoporous carbon supported copper based catalyst of this invention or a mesoporous carbon supported copper based catalyst produced by the aforesaid process of this invention contacts with the $C_2$ to $C_{12}$ chain alkyl compound (or a mixture feed of the $C_2$ to $C_{12}$ chain alkyl compound with $CO_2$), to convert the $C_2$ to $C_{12}$ chain alkyl group into its corresponding chain alkenyl group by a catalytic dehydrogenation reaction.

The contacting could be conducted by any means known in this field (for example, how to conduct the contacting reaction, what kind of reactor to be involved, how to introduce the catalyst or the $C_2$ to $C_{12}$ chain alkyl compound or the mixture feed, and etc.), no need to repeatedly describe herein, except for that specified herein below as to the catalytic dehydrogenation reaction conditions.

According to this invention, the catalytic dehydrogenation reaction conditions include: a reaction temperature of 450-700° C., preferably 520-650° C., a reaction pressure of 0.05-10.0 MPa, preferably 0.8-1.0 MPa, a space velocity of 0.5-40 $Lg^{-1}_{cat}h^{-1}$, preferably 1-10 $Lg^{-1}_{cat}h^{-1}$. When a mixture feed is used, the ratio by molar of the $C_2$ to $C_{12}$ chain alkyl compound (for example, ethane, propane, isobutane, iso-pentane, ethyl benzene, ethyl cyclohexane or any combination thereof) to $CO_2$ is 1:0.1 to 1:40, preferably 1:0.5 to 1:20.

If needed, before contacting with the catalyst, the $C_2$ to $C_{12}$ chain alkyl compound or the mixture feed may be preheated to 250-600° C., such as 320-500° C.

According to this invention, when the $C_2$ to $C_{12}$ chain alkyl compound carries only one single $C_2$ to $C_{12}$ chain alkyl group, the one single $C_2$ to $C_{12}$ chain alkyl group is catalytically dehydrogenated. When the $C_2$ to $C_{12}$ chain alkyl compound carries two or more $C_2$ to $C_{12}$ chain alkyl groups, it is envisaged that at least one (or all, but unnecessarily) of the two or more $C_2$ to $C_{12}$ chain alkyl groups is catalytically dehydrogenated, while if needed in some case, all of the two or more $C_2$ to $C_{12}$ chain alkyl groups may be catalytically dehydrogenated.

Further, the catalytic dehydrogenation reaction generally removes two hydrogen atoms from the $C_2$ to $C_{12}$ chain alkyl group and converts same into the corresponding $C_2$ to $C_{12}$ chain alkenyl group. As a result, the thus obtained $C_2$ to $C_{12}$ chain alkenyl group generally contains only one carbon-carbon double bond, but not limiting thereto. There is no specific limitation as to the position of the carbon-carbon double bond on the $C_2$ to $C_{12}$ chain alkenyl group, for example, the terminal or a position adjacent to the terminal of the $C_2$ to $C_{12}$ chain alkenyl group, but not limiting thereto.

According to a specific embodiment of this invention, the $C_2$ to $C_{12}$ chain alkyl compound is isobutane. To this end, according to this invention, further provided is a process for producing isobutene, characterized by comprising a step of contacting the aforesaid mesoporous carbon supported copper based catalyst of this invention or a mesoporous carbon supported copper based catalyst produced by the aforesaid process of this invention with a mixture feed of isobutane with $CO_2$, to convert isobutane into isobutene by a catalytic dehydrogenation reaction.

According to this invention, the isobutane catalytic dehydrogenation reaction conditions preferably include: a reaction temperature of 550-650° C., preferably 560-610° C., a reaction pressure of 0.05-1.0 MPa, preferably 0.06-0.5 MPa, a space velocity of 0.5-8 $Lg^{-1}_{cat}h^{-1}$, the ratio by molar of isobutane to $CO_2$ is 1:0.5 to 1:11. If needed, before contacting with the catalyst, the mixture feed may be preheated to 300-500° C., such as 320-450° C.

EXAMPLES

This invention will be described in further details with reference to the following examples, but by no means be limited to same.

Example 1

42.4 g copper(II) nitrate and 44.6 g citric acid were dissolved in 600 ml water, to obtain a mixture solution, and then into said solution, 158.8 g CMK-3, a mesoporous carbon having a specific surface area of 1320 $m^2 g^{-1}$ and a most probable pore size of 4.3 nm, was introduced. Then, the mixture was stirred for 10 min in a thermostatic water bath at 70° C., dried at 150° C., calcined at 680° C. under a nitrogen gas atmosphere for 5 hours, to obtained a mesoporous carbon supported copper based catalyst, which has a measured CuO amount by weight of 9.9%. The catalyst was loaded into a fixed-bed reactor, and to said reactor, a mixture feed, preheated to 340° C., of isobutane and $CO_2$ with a ratio by molar of isobutane to $CO_2$ is 1:6 was supplied, to react under the following reaction conditions: a reaction temperature of 630° C., a reaction pressure of 0.1 MPa, and a space velocity of 5 $Lg^{-1}_{cat}h^{-1}$. As a result, the conversion of isobutane measured at 1 hour after the beginning of the reaction is 58% and the selectivity to isobutene is 88.6%, while the conversion of isobutane measured at 3 hour after the beginning of the reaction is 48% and the selectivity to isobutene is 89.2%.

Comparative Example 1

42.4 g copper(II) nitrate and 44.6 g citric acid were dissolved in 600 ml water, to obtain a mixture solution, and then into said solution, 158.8 g activated carbon having a specific surface area of 1420 $m^2 g^{-1}$ and a most probable pore size of 0.8 nm was introduced. Then, the mixture was stirred for 10 min in a thermostatic water bath at 70° C., dried at 150° C., calcined at 680° C. under a nitrogen gas atmosphere for 5 hours, to obtained an activated carbon supported copper based catalyst, which has a measured CuO amount by weight of 10.1%. The catalyst was loaded into a fixed-bed reactor, and to said reactor, a mixture feed, preheated to 340° C., of isobutane and $CO_2$ with a ratio by molar of isobutane to $CO_2$ is 1:6 was supplied, to react under the following reaction conditions: a reaction temperature of 630° C., a reaction pressure of 0.1 MPa, and a space velocity of 5 $Lg^{-1}_{cat}h^{-1}$. As a result, the conversion of isobutane measured at 1 hour after the beginning of the reaction is 33% and the selectivity to isobutene is 89.1%, while the conversion of isobutane measured at 3 hour after the beginning of the reaction is 14% and the selectivity to isobutene is 90.2%.

Example 2

10.0 g copper(II) acetate and 20.1 g citric acid were dissolved in 1150 ml water, to obtain a mixture solution, and then into said solution, 214.5 g disordered mesoporous carbon having a specific surface area of 1230 $m^2 g^{-1}$ and a most probable pore size of 6.0 nm (produced according to Journal of Materials Chemistry, Vol. 19, 2009, pp. 7759-7764) was introduced. Then, the mixture was stirred for 10 min in a thermostatic water bath at 70° C., dried at 120° C., calcined at 680° C. under a nitrogen gas atmosphere for 5 hours, to obtained a mesoporous carbon supported copper based catalyst, which has a measured CuO amount by weight of 2.0%. The catalyst was loaded into a fixed-bed reactor, and to said reactor, a mixture feed, preheated to 300° C., of isobutane and $CO_2$ with a ratio by molar of isobutane to $CO_2$ is 1:4 was supplied, to react under the following reaction conditions: a reaction temperature of 630° C., a reaction pressure of 0.1 MPa, and a space velocity of 4 $Lg^{-1}{}_{cat}h^{-1}$. As a result, the conversion of isobutane measured at 1 hour after the beginning of the reaction is 37% and the selectivity to isobutene is 89.0%, while the conversion of isobutane measured at 3 hour after the beginning of the reaction is 24% and the selectivity to isobutene is 91.2%.

Example 3

21.4 g copper(II) nitrate and 38.6 g citric acid were dissolved in 600 ml water, to obtain a mixture solution, and then into said solution, 158.8 g disordered mesoporous carbon having a specific surface area of 1230 $m^2 g^{-1}$ and a most probable pore size of 6.0 nm (produced according to Journal of Materials Chemistry, Vol. 19, 2009, pp. 7759-7764) was introduced. Then, the mixture was stirred for 10 min in a thermostatic water bath at 70° C., dried at 120° C., calcined at 680° C. under a nitrogen gas atmosphere for 3 hours, to obtained a mesoporous carbon supported copper based catalyst, which has a measured CuO amount by weight of 5.0%. The catalyst was loaded into a fixed-bed reactor, and to said reactor, a mixture feed, preheated to 340° C., of isobutane and $CO_2$ with a ratio by molar of isobutane to $CO_2$ is 1:6 was supplied, to react under the following reaction conditions: a reaction temperature of 630° C., a reaction pressure of 0.1 MPa, and a space velocity of 5 $Lg^{-1}{}_{cat}h^{-1}$. As a result, the conversion of isobutane measured at 1 hour after the beginning of the reaction is 48% and the selectivity to isobutene is 90.4%, while the conversion of isobutane measured at 3 hour after the beginning of the reaction is 38% and the selectivity to isobutene is 91.2%.

Example 4

74.4 g copper(II) chloride and 30.4 g citric acid were dissolved in 600 ml water, to obtain a mixture solution, and then into said solution, 176.8 g disordered mesoporous carbon having a specific surface area of 1230 $m^2 g^{-1}$ and a most probable pore size of 6.0 nm (produced according to Journal of Materials Chemistry, Vol. 19, 2009, pp. 7759-7764) was introduced. Then, the mixture was stirred for 10 min in a thermostatic water bath at 70° C., dried at 120° C., calcined at 680° C. under a nitrogen gas atmosphere for 5 hours, to obtained a mesoporous carbon supported copper based catalyst, which has a measured CuO amount by weight of 20.0%. The catalyst was loaded into a fixed-bed reactor, and to said reactor, a mixture feed, preheated to 300° C., of isobutane and $CO_2$ with a ratio by molar of isobutane to $CO_2$ is 1:4 was supplied, to react under the following reaction conditions: a reaction temperature of 630° C., a reaction pressure of 0.1 MPa, and a space velocity of 4 $Lg^{-1}{}_{cat}h^{-1}$. As a result, the conversion of isobutane measured at 1 hour after the beginning of the reaction is 42% and the selectivity to isobutene is 86.0%, while the conversion of isobutane measured at 3 hour after the beginning of the reaction is 30% and the selectivity to isobutene is 89.5%.

Example 5

12.7 g copper(II) nitrate, 0.5 g $SnCl_2$ and 5.1 g citric acid were dissolved in 2149 ml water, to obtain a mixture solution, and then into said solution, 173.2 g CMK-3, a mesoporous carbon having a specific surface area of 1320 $m^2 g^{-1}$ and a most probable pore size of 4.3 nm, was introduced. Then, the mixture was stirred for 10 min in a thermostatic water bath at 70° C., dried at 120° C., calcined at 690° C. under a nitrogen gas atmosphere for 3 hours, to obtained a mesoporous carbon supported copper based catalyst, which has a measured CuO amount by weight of 3.0% and a measured $SnO_2$ amount by weight of 0.2%. The catalyst was loaded into a fixed-bed reactor, and to said reactor, a mixture feed, preheated to 320° C., of isobutane and $CO_2$ with a ratio by molar of isobutane to $CO_2$ is 1:11 was supplied, to react under the following reaction conditions: a reaction temperature of 600° C., a reaction pressure of 0.1 MPa, and a space velocity of 5 $Lg^{-1}{}_{cat}h^{-1}$. As a result, the conversion of isobutane measured at 1 hour after the beginning of the reaction is 52% and the selectivity to isobutene is 89.7%, while the conversion of isobutane measured at 3 hour after the beginning of the reaction is 43% and the selectivity to isobutene is 90.5%.

Reference Example 1

12.6 g copper(II) nitrate and 5.1 g citric acid were dissolved in 2149 ml water, to obtain a mixture solution, and then into said solution, 173.2 g CMK-3, a mesoporous carbon having a specific surface area of 1320 $m^2 g^{-1}$ and a most probable pore size of 4.3 nm, was introduced. Then, the mixture was stirred for 10 min in a thermostatic water bath at 70° C., dried at 120° C., calcined at 680° C. under a nitrogen gas atmosphere for 5 hours, to obtained a mesoporous carbon supported copper based catalyst, which has a measured CuO amount by weight of 3.0%. The catalyst was loaded into a fixed-bed reactor, and to said reactor, a mixture feed, preheated to 320° C., of isobutane and $CO_2$ with a ratio by molar of isobutane to $CO_2$ is 1:11 was supplied, to react under the following reaction conditions: a reaction temperature of 610° C., a reaction pressure of 0.1 MPa, and a space velocity of 5 $Lg^{-1}{}_{cat}h^{-1}$. As a result, the conversion of isobutane measured at 1 hour after the beginning of the reaction is 48% and the selectivity to isobutene is 90.3%, while the conversion of isobutane measured at 3 hour after the beginning of the reaction is 31% and the selectivity to isobutene is 90.8%.

Example 6

26.0 g copper(II) nitrate, 1.4 g $SnCl_2$ and 26.0 g citric acid were dissolved in 2149 ml water, to obtain a mixture solution, and then into said solution, 207.6 g CMK-3, a mesoporous carbon having a specific surface area of 1320 $m^2 g^{-1}$ and a most probable pore size of 4.3 nm, was introduced. Then, the mixture was stirred for 10 min in a thermostatic water bath at 70° C., dried at 80° C., calcined at 610° C. under a nitrogen gas atmosphere for 8 hours, to obtained a mesoporous carbon supported copper based catalyst, which has a measured CuO amount by weight of 5.1% and a measured $SnO_2$ amount by weight of 0.5%. The catalyst was loaded into a fixed-bed reactor, and to said reactor, a mixture feed, preheated to 340° C., of isobutane and $CO_2$ with a ratio by molar of isobutane to $CO_2$ is 1:6 was supplied, to react under the following reaction conditions: a reaction temperature of 600° C., a reaction pressure of 0.1 MPa, and a space velocity of 3 $Lg^{-1}{}_{cat}h^{-1}$. As a result, the conversion of isobutane measured at 1 hour after the beginning of the reaction is 57% and the selectivity to isobutene is 85.3%, while the conversion of isobutane measured at 3 hour after the beginning of the reaction is 52% and the selectivity to isobutene is 89.4%.

Example 7

27.5 g copper(II) acetate, 1.7 g $SnSO_4$ and 55.0 g citric acid were dissolved in 600 ml water, to obtain a mixture solution, and then into said solution, 105.6 g CMK-3, a mesoporous carbon having a specific surface area of 1320 m$^2$ g$^{-1}$ and a most probable pore size of 4.3 nm, was introduced. Then, the mixture was stirred for 10 min in a thermostatic water bath at 70° C., dried at 100° C., calcined at 680° C. under a nitrogen gas atmosphere for 5 hours, to obtained a mesoporous carbon supported copper based catalyst, which has a measured CuO amount by weight of 9.9% and a measured SnO$_2$ amount by weight of 0.9%. The catalyst was loaded into a fluidized-bed reactor, and to said reactor, a mixture feed, preheated to 450° C., of isobutane and CO$_2$ with a ratio by molar of isobutane to CO$_2$ is 1:4 was supplied, to react under the following reaction conditions: a reaction temperature of 600° C., a reaction pressure of 0.1 MPa, and a space velocity of 3 Lg$^{-1}_{cat}$h$^{-1}$. As a result, the conversion of isobutane measured at 1 hour after the beginning of the reaction is 62% and the selectivity to isobutene is 88.7%, while the conversion of isobutane measured at 3 hour after the beginning of the reaction is 56% and the selectivity to isobutene is 89.9%.

Example 8

20.2 g copper(II) chloride, 2.6 g SnSO$_4$, and 40.0 g citric acid were dissolved in 700 ml water, to obtain a mixture solution, and then into said solution, 105.6 g disordered mesoporous carbon having a specific surface area of 1230 m$^2$ g$^{-1}$ and a most probable pore size of 6.0 nm (produced according to Journal of Materials Chemistry, Vol. 19, 2009, pp. 7759-7764) was introduced. Then, the mixture was stirred for 10 min in a thermostatic water bath at 70° C., dried at 100° C., calcined at 680° C. under a nitrogen gas atmosphere for 3 hours, to obtained a mesoporous carbon supported copper based catalyst, which has a measured CuO amount by weight of 10.1% and a measured SnO$_2$ amount by weight of 1.5%. The catalyst was loaded into a fixed-bed reactor, and to said reactor, a mixture feed, preheated to 380° C., of isobutane and CO$_2$ with a ratio by molar of isobutane to CO$_2$ is 1:2 was supplied, to react under the following reaction conditions: a reaction temperature of 610° C., a reaction pressure of 0.1 MPa, and a space velocity of 5 Lg$^{-1}_{cat}$h$^{-1}$. As a result, the conversion of isobutane measured at 1 hour after the beginning of the reaction is 68% and the selectivity to isobutene is 83.9%, while the conversion of isobutane measured at 3 hour after the beginning of the reaction is 59% and the selectivity to isobutene is 90.8%.

Example 9

34.6 g copper(II) acetate, 2.9 g SnCl$_2$ and 26.0 g citric acid were dissolved in 1000 ml water, to obtain a mixture solution, and then into said solution, 98.7 g commercial available mesoporous carbon (LD-7, Nanjing Linda Activated Carbon Co., Ltd) having a specific surface area of 980 m$^2$ g$^{-1}$ and a most probable pore size of 2.2 nm was introduced. Then, the mixture was stirred for 10 min in a thermostatic water bath at 70° C., dried at 110° C., calcined at 560° C. under a nitrogen gas atmosphere for 5 hours, to obtained a mesoporous carbon supported copper based catalyst, which has a measured CuO amount by weight of 12.9% and a measured SnO$_2$ amount by weight of 2.0%. The catalyst was loaded into a fixed-bed reactor, and to said reactor, a mixture feed, preheated to 320° C., of isobutane and CO$_2$ with a ratio by molar of isobutane to CO$_2$ is 1:0.5 was supplied, to react under the following reaction conditions: a reaction temperature of 550° C., a reaction pressure of 0.1 MPa, and a space velocity of 8 Lg$^{-1}_{cat}$h$^{-1}$. As a result, the conversion of isobutane measured at 1 hour after the beginning of the reaction is 38% and the selectivity to isobutene is 96.7%, while the conversion of isobutane measured at 3 hour after the beginning of the reaction is 35% and the selectivity to isobutene is 98.1%.

Example 10

43.6 g copper(II) nitrate, 2.1 g SnCl$_2$ and 44.6 g citric acid were dissolved in 650 ml water, to obtain a mixture solution, and then into said solution, 103.4 g commercial available mesoporous carbon (LD-7, Nanjing Linda Activated Carbon Co., Ltd) having a specific surface area of 980 m$^2$ g$^{-1}$ and a most probable pore size of 2.2 nm was introduced. Then, the mixture was stirred for 10 min in a thermostatic water bath at 70° C., dried at 100° C., calcined at 640° C. under a nitrogen gas atmosphere for 5 hours, to obtained a mesoporous carbon supported copper based catalyst, which has a measured CuO amount by weight of 15.0% and a measured SnO$_2$ amount by weight of 1.5%. The catalyst was loaded into a fixed-bed reactor, and to said reactor, a mixture feed, preheated to 340° C., of isobutane and CO$_2$ with a ratio by molar of isobutane to CO$_2$ is 1:8 was supplied, to react under the following reaction conditions: a reaction temperature of 610° C., a reaction pressure of 0.1 MPa, and a space velocity of 5 Lg$^{-1}_{cat}$h$^{-1}$. As a result, the conversion of isobutane measured at 1 hour after the beginning of the reaction is 70% and the selectivity to isobutene is 87.1%, while the conversion of isobutane measured at 3 hour after the beginning of the reaction is 61% and the selectivity to isobutene is 89.3%.

Example 11

26.0 g copper(II) nitrate, 1.4 g ammonium meta-vanadate and 26.0 g citric acid were dissolved in 800 ml water, to obtain a mixture solution, and then into said solution, 230.6 g CMK-3, a mesoporous carbon having a specific surface area of 1320 m$^2$ g$^{-1}$ and a most probable pore size of 4.3 nm, was introduced. Then, the mixture was stirred for 10 min in a thermostatic water bath at 70° C., dried at 80° C., calcined at 630° C. under a nitrogen gas atmosphere for 8 hours, to obtained a mesoporous carbon supported copper based catalyst, which has a measured CuO amount by weight of 4.3% and a measured V$_2$O$_5$ amount by weight of 0.4%. The catalyst was loaded into a fluidized-bed reactor, and to said reactor, a mixture feed, preheated to 340° C., of isobutane and CO$_2$ with a ratio by molar of isobutane to CO$_2$ is 1:6 was supplied, to react under the following reaction conditions: a reaction temperature of 600° C., a reaction pressure of 0.1 MPa, and a space velocity of 2 Lg$^{-1}_{cat}$h$^{-1}$. As a result, the conversion of isobutane measured at 1 hour after the beginning of the reaction is 51% and the selectivity to isobutene is 86.1%, while the conversion of isobutane measured at 3 hour after the beginning of the reaction is 43% and the selectivity to isobutene is 89.3%.

Example 12

30.3 g copper(II) chloride, 13.3 g LiNO$_3$ and 44.6 g citric acid were dissolved in 600 ml water, to obtain a mixture solution, and then into said solution, 158.8 g CMK-3, a mesoporous carbon having a specific surface area of 1320 m$^2$ g$^{-1}$ and a most probable pore size of 4.3 nm, was introduced. Then, the mixture was stirred for 10 min in a thermostatic water bath at 70° C., dried at 150° C., calcined at 680° C. under a nitrogen gas atmosphere for 5 hours, to obtained a mesoporous carbon supported copper based catalyst, which has a measured CuO amount by weight of 9.7% and a measured Li$_2$O amount by weight of 1.6%. The catalyst was loaded into a fixed-bed reactor, and to said reactor, a mixture feed, preheated to 340° C., of isobutane and $CO_2$ with a ratio by molar of isobutane to $CO_2$ is 1:6 was supplied, to react under the following reaction conditions: a reaction temperature of 600° C., a reaction pressure of 0.1 MPa, and a space velocity of 1 $Lg^{-1}{}_{cat}h^{-1}$. As a result, the conversion of isobutane measured at 1 hour after the beginning of the reaction is 59% and the selectivity to isobutene is 91.2%, while the conversion of isobutane measured at 3 hour after the beginning of the reaction is 55% and the selectivity to isobutene is 91.6%.

Example 13

30.3 g copper(II) nitrate, 19.3 g $LiNO_3$ and 44.6 g citric acid were dissolved in 800 ml water, to obtain a mixture solution, and then into said solution, 158.8 g CMK-3, a mesoporous carbon having a specific surface area of 1320 $m^2 g^{-1}$ and a most probable pore size of 4.3 nm, was introduced. Then, the mixture was stirred for 10 min in a thermostatic water bath at 70° C., dried at 150° C., calcined at 670° C. under a nitrogen gas atmosphere for 5 hours, to obtained a mesoporous carbon supported copper based catalyst, which has a measured CuO amount by weight of 7.8% and a measured $Li_2O$ amount by weight of 2.1%. The catalyst was loaded into a fixed-bed reactor, and to said reactor, a mixture feed, preheated to 340° C., of isobutane and $CO_2$ with a ratio by molar of isobutane to $CO_2$ is 1:6 was supplied, to react under the following reaction conditions: a reaction temperature of 600° C., a reaction pressure of 0.1 MPa, and a space velocity of 2 $Lg^{-1}{}_{cat}h^{-1}$. As a result, the conversion of isobutane measured at 1 hour after the beginning of the reaction is 56% and the selectivity to isobutene is 92.4%, while the conversion of isobutane measured at 3 hour after the beginning of the reaction is 51% and the selectivity to isobutene is 92.7%.

Example 14

38.3 g copper(II) nitrate, 5.2 g $LiNO_3$ and 49.6 g citric acid were dissolved in 700 ml water, to obtain a mixture solution, and then into said solution, 152.7 g CMK-3, a mesoporous carbon having a specific surface area of 1320 $m^2 g^{-1}$ and a most probable pore size of 4.3 nm, was introduced. Then, the mixture was stirred for 10 min in a thermostatic water bath at 70° C., dried at 150° C., calcined at 680° C. under a nitrogen gas atmosphere for 5 hours, to obtained a mesoporous carbon supported copper based catalyst, which has a measured CuO amount by weight of 9.2% and a measured $Li_2O$ amount by weight of 0.5%. The catalyst was loaded into a fixed-bed reactor, and to said reactor, a mixture feed, preheated to 350° C., of isobutane and $CO_2$ with a ratio by molar of isobutane to $CO_2$ is 1:10 was supplied, to react under the following reaction conditions: a reaction temperature of 600° C., a reaction pressure of 0.1 MPa, and a space velocity of 1 $Lg^{-1}{}_{cat}h^{-1}$. As a result, the conversion of isobutane measured at 1 hour after the beginning of the reaction is 57% and the selectivity to isobutene is 90.4%, while the conversion of isobutane measured at 3 hour after the beginning of the reaction is 53% and the selectivity to isobutene is 91.2%.

Example 15

19.0 g copper(II) nitrate, 1.4 g $Mg(NO_3)_2$ and 26.0 g citric acid were dissolved in 2149 ml water, to obtain a mixture solution, and then into said solution, 210.2 g CMK-3, a mesoporous carbon having a specific surface area of 1320 $m^2 g^{-1}$ and a most probable pore size of 4.3 nm, was introduced. Then, the mixture was stirred for 10 min in a thermostatic water bath at 70° C., dried at 80° C., calcined at 610° C. under a nitrogen gas atmosphere for 8 hours, to obtained a mesoporous carbon supported copper based catalyst, which has a measured CuO amount by weight of 3.5% and a measured MgO amount by weight of 0.9%. The catalyst was loaded into a moving bed reactor, and to said reactor, a mixture feed, preheated to 340° C., of isobutane and $CO_2$ with a ratio by molar of isobutane to $CO_2$ is 1:6 was supplied, to react under the following reaction conditions: a reaction temperature of 620° C., a reaction pressure of 0.1 MPa, and a space velocity of 2 $Lg^{-1}{}_{cat}h^{-1}$. As a result, the conversion of isobutane measured at 1 hour after the beginning of the reaction is 51% and the selectivity to isobutene is 85.3%, while the conversion of isobutane measured at 3 hour after the beginning of the reaction is 41% and the selectivity to isobutene is 86.2%.

Example 16

28.2 g copper(II) acetate, 2.1 g $CaCl_2$ and 31.0 g citric acid were dissolved in 1000 ml water, to obtain a mixture solution, and then into said solution, 220.3 g commercial available mesoporous carbon (LD-7, Nanjing Linda Activated Carbon Co., Ltd) having a specific surface area of 980 $m^2 g^{-1}$ and a most probable pore size of 2.2 nm was introduced. Then, the mixture was stirred for 10 min in a thermostatic water bath at 70° C., dried at 110° C., calcined at 560° C. under a nitrogen gas atmosphere for 5 hours, to obtained a mesoporous carbon supported copper based catalyst, which has a measured CuO amount by weight of 4.9% and a measured CaO amount by weight of 0.4%. The catalyst was loaded into a fixed-bed reactor, and to said reactor, a mixture feed, preheated to 320° C., of isobutane and $CO_2$ with a ratio by molar of isobutane to $CO_2$ is 1:9 was supplied, to react under the following reaction conditions: a reaction temperature of 620° C., a reaction pressure of 0.1 MPa, and a space velocity of 10 $Lg^{-1}{}_{cat}h^{-1}$. As a result, the conversion of isobutane measured at 1 hour after the beginning of the reaction is 50% and the selectivity to isobutene is 87.1%, while the conversion of isobutane measured at 3 hour after the beginning of the reaction is 40% and the selectivity to isobutene is 88.4%.

Example 17

19.2 g copper(II) nitrate, 3.5 g gallium(III) nitrate and 34.6 g citric acid were dissolved in 650 ml water, to obtain a mixture solution, and then into said solution, 197.6 g commercial available mesoporous carbon (LD-7, Nanjing Linda Activated Carbon Co., Ltd) having a specific surface area of 980 $m^2 g^{-1}$ and a most probable pore size of 2.2 nm was introduced. Then, the mixture was stirred for 10 min in a thermostatic water bath at 70° C., dried at 100° C., calcined at 640° C. under a nitrogen gas atmosphere for 5 hours, to obtained a mesoporous carbon supported copper based catalyst, which has a measured CuO amount by weight of 3.8% and a measured $Ga_2O_3$ amount by weight of 0.4%. The catalyst was loaded into a fixed-bed reactor, and to said reactor, a mixture feed, preheated to 340° C., of isobutane and $CO_2$ with a ratio by molar of isobutane to $CO_2$ is 1:8 was supplied, to react under the following reaction conditions: a reaction temperature of 620° C., a reaction pressure of 0.1 MPa, and a space velocity of 3 $Lg^{-1}{}_{cat}h^{-1}$. As a result, the conversion of isobutane measured at 1 hour after the beginning of the reaction is 54% and the selectivity to isobutene is 86.7%, while the conversion of isobutane measured at 3 hour after the beginning of the reaction is 48% and the selectivity to isobutene is 88.1%.

Example 18

21.6 g copper(II) nitrate, 4.2 g $Zn(NO_3)_2$ and 40.6 g citric acid were dissolved in 650 ml water, to obtain a mixture solution, and then into said solution, 103.4 g commercial available mesoporous carbon (LD-7, Nanjing Linda Activated Carbon Co., Ltd) having a specific surface area of 980 $m^2 g^{-1}$ and a most probable pore size of 2.2 nm was introduced. Then, the mixture was stirred for 10 min in a thermostatic water bath at 70° C., dried at 100° C., calcined at 640° C. under a nitrogen gas atmosphere for 5 hours, to obtained a mesoporous carbon supported copper based catalyst, which has a measured CuO amount by weight of 4.1% and a measured ZnO amount by weight of 0.8%. The catalyst was loaded into a fixed-bed reactor, and to said reactor, a mixture feed, preheated to 340° C., of isobutane and $CO_2$ with a ratio by molar of isobutane to $CO_2$ is 1:10 was supplied, to react under the following reaction conditions: a reaction temperature of 610° C., a reaction pressure of 0.1 MPa, and a space velocity of 3 $Lg^{-1}_{cat}h^{-1}$. As a result, the conversion of isobutane measured at 1 hour after the beginning of the reaction is 55% and the selectivity to isobutene is 85.1%, while the conversion of isobutane measured at 3 hour after the beginning of the reaction is 48% and the selectivity to isobutene is 88.6%.

Example 19

34.0 g copper(II) nitrate, 4.1 g $Al(NO_3)_3$ and 19.2 g citric acid were dissolved in 650 ml water, to obtain a mixture solution, and then into said solution, 240.1 g CMK-3, a mesoporous carbon having a specific surface area of 1320 $m^2 g^{-1}$ and a most probable pore size of 4.3 nm, was introduced. Then, the mixture was stirred for 10 min in a thermostatic water bath at 70° C., dried at 100° C., calcined at 640° C. under a nitrogen gas atmosphere for 5 hours, to obtained a mesoporous carbon supported copper based catalyst, which has a measured CuO amount by weight of 5.8% and a measured $Al_2O_3$ amount by weight of 0.3%. The catalyst was loaded into a fixed-bed reactor, and to said reactor, a mixture feed, preheated to 390° C., of isobutane and $CO_2$ with a ratio by molar of isobutane to $CO_2$ is 1:10 was supplied, to react under the following reaction conditions: a reaction temperature of 620° C., a reaction pressure of 0.1 MPa, and a space velocity of 2 $Lg^{-1}_{cat}h^{-1}$. As a result, the conversion of isobutane measured at 1 hour after the beginning of the reaction is 59% and the selectivity to isobutene is 87.9%, while the conversion of isobutane measured at 3 hour after the beginning of the reaction is 50% and the selectivity to isobutene is 88.6%.

Example 20

29.2 g copper(II) nitrate, 2.0 g cerium(III) nitrate and 48.6 g citric acid were dissolved in 1200 ml water, to obtain a mixture solution, and then into said solution, 298.0 g CMK-3, a mesoporous carbon having a specific surface area of 1320 $m^2 g^{-1}$ and a most probable pore size of 4.3 nm, was introduced. Then, the mixture was stirred for 10 min in a thermostatic water bath at 70° C., dried at 100° C., calcined at 640° C. under a nitrogen gas atmosphere for 5 hours, to obtained a mesoporous carbon supported copper based catalyst, which has a measured CuO amount by weight of 3.7% and a measured $CeO_2$ amount by weight of 0.3%. The catalyst was loaded into a fixed-bed reactor, and to said reactor, a mixture feed, preheated to 340° C., of isobutane and $CO_2$ with a ratio by molar of isobutane to $CO_2$ is 1:9 was supplied, to react under the following reaction conditions: a reaction temperature of 600° C., a reaction pressure of 0.1 MPa, and a space velocity of 4 $Lg^{-1}_{cat}h^{-1}$. As a result, the conversion of isobutane measured at 1 hour after the beginning of the reaction is 62% and the selectivity to isobutene is 85.0%, while the conversion of isobutane measured at 3 hour after the beginning of the reaction is 55% and the selectivity to isobutene is 87.6%.

Example 21

22.2 g copper(II) nitrate, 2.0 g $LaCl_3$ and 24.6 g citric acid were dissolved in 1000 ml water, to obtain a mixture solution, and then into said solution, 298.0 g CMK-3, a mesoporous carbon having a specific surface area of 1320 $m^2 g^{-1}$ and a most probable pore size of 4.3 nm, was introduced. Then, the mixture was stirred for 10 min in a thermostatic water bath at 70° C., dried at 100° C., calcined at 640° C. under a nitrogen gas atmosphere for 5 hours, to obtained a mesoporous carbon supported copper based catalyst, which has a measured CuO amount by weight of 2.8% and a measured $La_2O_3$ amount by weight of 1.1%. The catalyst was loaded into a fixed-bed reactor, and to said reactor, a mixture feed, preheated to 340° C., of isobutane and $CO_2$ with a ratio by molar of isobutane to $CO_2$ is 1:10 was supplied, to react under the following reaction conditions: a reaction temperature of 630° C., a reaction pressure of 0.1 MPa, and a space velocity of 2 $Lg^{-1}_{cat}h^{-1}$. As a result, the conversion of isobutane measured at 1 hour after the beginning of the reaction is 69% and the selectivity to isobutene is 84.8%, while the conversion of isobutane measured at 3 hour after the beginning of the reaction is 59% and the selectivity to isobutene is 86.6%.

Example 22

42.4 g copper(II) nitrate, 4.0 g $KNO_3$ and 44.6 g citric acid were dissolved in 600 ml water, to obtain a mixture solution, and then into said solution, 158.8 g CMK-3, a mesoporous carbon having a specific surface area of 1320 $m^2 g^{-1}$ and a most probable pore size of 4.3 nm, was introduced. Then, the mixture was stirred for 10 min in a thermostatic water bath at 70° C., dried at 150° C., calcined at 670° C. under a nitrogen gas atmosphere for 5 hours, to obtained a mesoporous carbon supported copper based catalyst, which has a measured CuO amount by weight of 9.9% and a measured $K_2O$ amount by weight of 0.9%. The catalyst was loaded into a fixed-bed reactor, and to said reactor, a mixture feed, preheated to 340° C., of isobutane and $CO_2$ with a ratio by molar of isobutane to $CO_2$ is 1:4 was supplied, to react under the following reaction conditions: a reaction temperature of 610° C., a reaction pressure of 0.1 MPa, and a space velocity of 2 $Lg^{-1}_{cat}h^{-1}$. As a result, the conversion of isobutane measured at 1 hour after the beginning of the reaction is 55% and the selectivity to isobutene is 90.4%, while the conversion of isobutane measured at 3 hour after the beginning of the reaction is 51% and the selectivity to isobutene is 90.6%.

Example 23

34.8 g copper(II) nitrate, 9.8 g $KNO_3$ and 44.6 g citric acid were dissolved in 600 ml water, to obtain a mixture solution, and then into said solution, 188.2 g CMK-3, a mesoporous carbon having a specific surface area of 1320 $m^2 g^{-1}$ and a most probable pore size of 4.3 nm, was introduced. Then, the mixture was stirred for 10 min in a thermostatic water bath at 80° C., dried at 120° C., calcined at 660° C. under a nitrogen gas atmosphere for 6 hours, to obtained a mesoporous carbon supported copper based catalyst, which has a measured CuO amount by weight of 7.5% and a measured $K_2O$ amount by weight of 2.1%. The catalyst was loaded into a fixed-bed reactor, and to said reactor, a mixture feed, preheated to 340° C., of isobutane and $CO_2$ with a ratio by molar of isobutane to $CO_2$ is 1:10 was supplied, to react under the following reaction conditions: a reaction temperature of 610° C., a reaction pressure of 0.1 MPa, and a space velocity of 1 $Lg^{-1}{}_{cat}h^{-1}$. As a result, the conversion of isobutane measured at 1 hour after the beginning of the reaction is 51% and the selectivity to isobutene is 91.1%, while the conversion of isobutane measured at 3 hour after the beginning of the reaction is 46% and the selectivity to isobutene is 91.7%.

Example 24

12.7 g copper(II) nitrate, 0.9 g $SnCl_2$, 1.2 g $LiNO_3$ and 7.1 g citric acid were dissolved in 2149 ml water, to obtain a mixture solution, and then into said solution, 173.2 g CMK-3, a mesoporous carbon having a specific surface area of 1320 $m^2$ $g^{-1}$ and a most probable pore size of 4.3 nm, was introduced. Then, the mixture was stirred for 10 min in a thermostatic water bath at 70° C., dried at 120° C., calcined at 690° C. under a nitrogen gas atmosphere for 3 hours, to obtained a mesoporous carbon supported copper based catalyst, which has a measured CuO amount by weight of 3.0%, a measured $SnO_2$ amount by weight of 0.3%, and a measured $Li_2O$ amount by weight of 0.1%. The catalyst was loaded into a fixed-bed reactor, and to said reactor, a mixture feed, preheated to 320° C., of isobutane and $CO_2$ with a ratio by molar of isobutane to $CO_2$ is 1:11 was supplied, to react under the following reaction conditions: a reaction temperature of 600° C., a reaction pressure of 0.1 MPa, and a space velocity of 3 $Lg^{-1}{}_{cat}h^{-1}$. As a result, the conversion of isobutane measured at 1 hour after the beginning of the reaction is 56% and the selectivity to isobutene is 90.7%, while the conversion of isobutane measured at 3 hour after the beginning of the reaction is 54% and the selectivity to isobutene is 91.2%.

Example 25

12.7 g copper(II) nitrate, 0.9 g $SnCl_2$, 1.2 g $KNO_3$ and 9.3 g citric acid were dissolved in 2149 ml water, to obtain a mixture solution, and then into said solution, 173.2 g CMK-3, a mesoporous carbon having a specific surface area of 1320 $m^2$ $g^{-1}$ and a most probable pore size of 4.3 nm, was introduced. Then, the mixture was stirred for 10 min in a thermostatic water bath at 70° C., dried at 120° C., calcined at 690° C. under a nitrogen gas atmosphere for 3 hours, to obtained a mesoporous carbon supported copper based catalyst, which has a measured CuO amount by weight of 3.0%, a measured $SnO_2$ amount by weight of 0.3%, and a measured $K_2O$ amount by weight of 0.3%. The catalyst was loaded into a fixed-bed reactor, and to said reactor, a mixture feed, preheated to 340° C., of isobutane and $CO_2$ with a ratio by molar of isobutane to $CO_2$ is 1:8 was supplied, to react under the following reaction conditions: a reaction temperature of 600° C., a reaction pressure of 0.1 MPa, and a space velocity of 1 $Lg^{-1}{}_{cat}h^{-1}$. As a result, the conversion of isobutane measured at 1 hour after the beginning of the reaction is 61% and the selectivity to isobutene is 91.7%, while the conversion of isobutane measured at 3 hour after the beginning of the reaction is 58% and the selectivity to isobutene is 92.3%.

Example 26

18.9 g copper(II) nitrate, 0.9 g $LiNO_3$, 1.2 g $KNO_3$ and 10.1 g citric acid were dissolved in 2000 ml water, to obtain a mixture solution, and then into said solution, 173.2 g CMK-3, a mesoporous carbon having a specific surface area of 1320 $m^2$ $g^{-1}$ and a most probable pore size of 4.3 nm, was introduced. Then, the mixture was stirred for 10 min in a thermostatic water bath at 70° C., dried at 120° C., calcined at 690° C. under a nitrogen gas atmosphere for 3 hours, to obtained a mesoporous carbon supported copper based catalyst, which has a measured CuO amount by weight of 4.1%, a measured $Li_2O$ amount by weight of 0.1% and a measured $K_2O$ amount by weight of 0.3%. The catalyst was loaded into a fixed-bed reactor, and to said reactor, a mixture feed, preheated to 320° C., of isobutane and $CO_2$ with a ratio by molar of isobutane to $CO_2$ is 1:5 was supplied, to react under the following reaction conditions: a reaction temperature of 610° C., a reaction pressure of 0.1 MPa, and a space velocity of 2 $Lg^{-1}{}_{cat}h^{-1}$. As a result, the conversion of isobutane measured at 1 hour after the beginning of the reaction is 59% and the selectivity to isobutene is 87.7%, while the conversion of isobutane measured at 3 hour after the beginning of the reaction is 56% and the selectivity to isobutene is 92.3%.

Example 27

18.9 g copper(II) nitrate, 1.8 g $SnCl_2$, 2.4 g $LiNO_3$, 2.7 g $KNO_3$ and 20.1 g citric acid were dissolved in 2000 ml water, to obtain a mixture solution, and then into said solution, 148.8 g CMK-3, a mesoporous carbon having a specific surface area of 1320 $m^2$ $g^{-1}$ and a most probable pore size of 4.3 nm, was introduced. Then, the mixture was stirred for 10 min in a thermostatic water bath at 70° C., dried at 120° C., calcined at 630° C. under a nitrogen gas atmosphere for 3 hours, to obtained a mesoporous carbon supported copper based catalyst, which has a measured CuO amount by weight of 4.6%, a measured $SnO_2$ amount by weight of 0.8%, a measured $Li_2O$ amount by weight of 0.3% and a measured $K_2O$ amount by weight of 0.7%. The catalyst was loaded into a fixed-bed reactor, and to said reactor, a mixture feed, preheated to 350° C., of isobutane and $CO_2$ with a ratio by molar of isobutane to $CO_2$ is 1:4 was supplied, to react under the following reaction conditions: a reaction temperature of 610° C., a reaction pressure of 0.1 MPa, and a space velocity of 2 $Lg^{-1}{}_{cat}h^{-1}$. As a result, the conversion of isobutane measured at 1 hour after the beginning of the reaction is 61% and the selectivity to isobutene is 91.4%, while the conversion of isobutane measured at 3 hour after the beginning of the reaction is 59% and the selectivity to isobutene is 92.3%.

Example 28

37.5 g copper(II) nitrate and 48.7 g tartaric acid were dissolved in 600 ml water, to obtain a mixture solution, and then into said solution, 210.3 g CMK-3, a mesoporous carbon having a specific surface area of 1320 $m^2$ $g^{-1}$ and a most probable pore size of 4.3 nm, was introduced. Then, the mixture was stirred for 10 min in a thermostatic water bath at 70° C., dried at 140° C., calcined at 670° C. under a nitrogen gas atmosphere for 5 hours, to obtained a mesoporous carbon supported copper based catalyst, which has a measured CuO amount by weight of 6.8%. The catalyst was loaded into a fixed-bed reactor, and to said reactor, a mixture feed, preheated to 330° C., of ethane and $CO_2$ with a ratio by molar of ethane to $CO_2$ is 1:10 was supplied, to react under the following reaction conditions: a reaction temperature of 650° C., a reaction pressure of 0.08 MPa, and a space velocity of 4 $Lg^{-1}{}_{cat}h^{-1}$. As a result, the conversion of ethane measured at 1 hour after the beginning of the reaction is 65% and the selectivity to ethene is 69.6%, while the conversion of ethane measured at 3 hour after the beginning of the reaction is 55% and the selectivity to ethene is 70.2%.

Example 29

42.2 g copper(II) nitrate, 4.2 g $KNO_3$ and 55.5 g ethylene glycol were dissolved in 600 ml water, to obtain a mixture solution, and then into said solution, 196.2 g CMK-3, a mesoporous carbon having a specific surface area of 1320 $m^2 g^{-1}$ and a most probable pore size of 4.3 nm, was introduced. Then, the mixture was stirred for 10 min in a thermostatic water bath at 70° C., dried at 150° C., calcined at 680° C. under a nitrogen gas atmosphere for 5 hours, to obtained a mesoporous carbon supported copper based catalyst, which has a measured CuO amount by weight of 8.1% and a measured $K_2O$ amount by weight of 0.8%. The catalyst was loaded into a fixed-bed reactor, and to said reactor, a mixture feed, preheated to 340° C., of ethane and $CO_2$ with a ratio by molar of ethane to $CO_2$ is 1:9 was supplied, to react under the following reaction conditions: a reaction temperature of 650° C., a reaction pressure of 0.08 MPa, and a space velocity of 2 $Lg^{-1}{}_{cat}h^{-1}$. As a result, the conversion of ethane measured at 1 hour after the beginning of the reaction is 74% and the selectivity to ethene is 71.1%, while the conversion of ethane measured at 3 hour after the beginning of the reaction is 71% and the selectivity to ethene is 71.6%.

Example 30

39.2 g copper(II) nitrate, 6.0 g cerium(III) nitrate and 51.6 g citric acid were dissolved in 1200 ml water, to obtain a mixture solution, and then into said solution, 285.0 g CMK-3, a mesoporous carbon having a specific surface area of 1320 $m^2 g^{-1}$ and a most probable pore size of 4.3 nm, was introduced. Then, the mixture was stirred for 10 min in a thermostatic water bath at 70° C., dried at 100° C., calcined at 660° C. under a nitrogen gas atmosphere for 5 hours, to obtained a mesoporous carbon supported copper based catalyst, which has a measured CuO amount by weight of 5.1% and a measured $CeO_2$ amount by weight of 1.0%. The catalyst was loaded into a fixed-bed reactor, and to said reactor, a mixture feed, preheated to 340° C., of ethane and $CO_2$ with a ratio by molar of ethane to $CO_2$ is 1:11 was supplied, to react under the following reaction conditions: a reaction temperature of 645° C., a reaction pressure of 0.1 MPa, and a space velocity of 1 $Lg^{-1}{}_{cat}h^{-1}$. As a result, the conversion of ethane measured at 1 hour after the beginning of the reaction is 72% and the selectivity to ethene is 68.1%, while the conversion of ethane measured at 3 hour after the beginning of the reaction is 67% and the selectivity to ethene is 68.8%.

Example 31

The catalyst produced in Example 25 was loaded into a fixed-bed reactor, and to said reactor, a mixture feed, preheated to 340° C., of ethane and $CO_2$ with a ratio by molar of ethane to $CO_2$ is 1:8 was supplied, to react under the following reaction conditions: a reaction temperature of 650° C., a reaction pressure of 0.1 MPa, and a space velocity of 1 $Lg^{-1}{}_{cat}h^{-1}$. As a result, the conversion of ethane measured at 1 hour after the beginning of the reaction is 72% and the selectivity to ethene is 70.3%, while the conversion of ethane measured at 3 hour after the beginning of the reaction is 68% and the selectivity to ethene is 71.2%.

Example 32

32.7 g copper(II) nitrate and 48.7 g glycerol were dissolved in 600 ml water, to obtain a mixture solution, and then into said solution, 158.8 g CMK-3, a mesoporous carbon having a specific surface area of 1320 $m^2 g^{-1}$ and a most probable pore size of 4.3 nm, was introduced. Then, the mixture was stirred for 10 min in a thermostatic water bath at 70° C., dried at 140° C., calcined at 660° C. under a nitrogen gas atmosphere for 6 hours, to obtained a mesoporous carbon supported copper based catalyst, which has a measured CuO amount by weight of 7.8%. The catalyst was loaded into a fixed-bed reactor, and to said reactor, a mixture feed, preheated to 330° C., of propane and $CO_2$ with a ratio by molar of propane to $CO_2$ is 1:10 was supplied, to react under the following reaction conditions: a reaction temperature of 580° C., a reaction pressure of 0.09 MPa, and a space velocity of 3 $Lg^{-1}{}_{cat}h^{-1}$. As a result, the conversion of propane measured at 1 hour after the beginning of the reaction is 27% and the selectivity to propene is 95.1%, while the conversion of propane measured at 3 hour after the beginning of the reaction is 22% and the selectivity to propene is 95.3%.

Example 33

29.6 g copper(II) chloride, 4.6 g $SnCl_2$ and 40.0 g ethylene glycol were dissolved in 1400 ml water, to obtain a mixture solution, and then into said solution, 210.2 g disordered mesoporous carbon having a specific surface area of 1230 $m^2 g^{-1}$ and a most probable pore size of 6.0 nm (produced according to Journal of Materials Chemistry, Vol. 19, 2009, pp. 7759-7764) was introduced. Then, the mixture was stirred for 10 min in a thermostatic water bath at 70° C., dried at 100° C., calcined at 660° C. under a nitrogen gas atmosphere for 5 hours, to obtained a mesoporous carbon supported copper based catalyst, which has a measured CuO amount by weight of 7.5% and a measured $SnO_2$ amount by weight of 1.5%. The catalyst was loaded into a fluidized-bed reactor, and to said reactor, a mixture feed, preheated to 380° C., of propane and $CO_2$ with a ratio by molar of propane to $CO_2$ is 1:10 was supplied, to react under the following reaction conditions: a reaction temperature of 590° C., a reaction pressure of 0.1 MPa, and a space velocity of 1 $Lg^{-1}{}_{cat}h^{-1}$. As a result, the conversion of propane measured at 1 hour after the beginning of the reaction is 33% and the selectivity to propene is 92.3%, while the conversion of propane measured at 3 hour after the beginning of the reaction is 26% and the selectivity to propene is 93.2%.

Example 34

23.6 g copper(II) nitrate, 9.2 g $Mg(NO_3)_2$ and 36.0 g citric acid were dissolved in 1600 ml water, to obtain a mixture solution, and then into said solution, 232.1 g disordered mesoporous carbon having a specific surface area of 1230 $m^2 g^{-1}$ and a most probable pore size of 6.0 nm (produced according to Journal of Materials Chemistry, Vol. 19, 2009, pp. 7759-7764) was introduced. Then, the mixture was stirred for 10 min in a thermostatic water bath at 70° C., dried at 80° C., calcined at 640° C. under a nitrogen gas atmosphere for 8 hours, to obtained a mesoporous carbon supported copper based catalyst, which has a measured CuO amount by weight of 4.0% and a measured MgO amount by weight of 1.6%. The catalyst was loaded into a moving bed reactor, and to said reactor, a mixture feed, preheated to 340° C., of propane and $CO_2$ with a ratio by molar of propane to $CO_2$ is 1:7 was supplied, to react under the following reaction conditions: a reaction temperature of 610° C., a reaction pressure of 0.1 MPa, and a space velocity of 1 $Lg^{-1}{}_{cat}h^{-1}$. As a result, the conversion of propane measured at 1 hour after the beginning of the reaction is 31% and the selectivity to propene is 93.3%, while the conversion of propane measured at 3 hour after the beginning of the reaction is 25% and the selectivity to propene is 93.6%.

Example 35

The catalyst produced in Example 26 was loaded into a fixed-bed reactor, and to said reactor, a mixture feed, preheated to 350° C., of propane and $CO_2$ with a ratio by molar of propane to $CO_2$ is 1:4 was supplied, to react under the following reaction conditions: a reaction temperature of 600° C., a reaction pressure of 0.1 MPa, and a space velocity of 2 $Lg^{-1}{}_{cat}h^{-1}$. As a result, the conversion of propane measured at 1 hour after the beginning of the reaction is 33% and the selectivity to propene is 94.1%, while the conversion of propane measured at 3 hour after the beginning of the reaction is 31% and the selectivity to propene is 94.6%.

Example 36

35.1 g copper(II) nitrate and 34.7 g ethylene glycol were dissolved in 1000 ml water, to obtain a mixture solution, and then into said solution, 200.1 g disordered mesoporous carbon having a specific surface area of 1230 $m^2 g^{-1}$ and a most probable pore size of 6.0 nm (produced according to Journal of Materials Chemistry, Vol. 19, 2009, pp. 7759-7764) was introduced. Then, the mixture was stirred for 10 min in a thermostatic water bath at 70° C., dried at 140° C., calcined at 660° C. under a nitrogen gas atmosphere for 6 hours, to obtained a mesoporous carbon supported copper based catalyst, which has a measured CuO amount by weight of 6.8%. The catalyst was loaded into a fixed-bed reactor, and to said reactor, a mixture feed, preheated to 330° C., of isopentane and $CO_2$ with a ratio by molar of isopentane to $CO_2$ is 1:5 was supplied, to react under the following reaction conditions: a reaction temperature of 560° C., a reaction pressure of 0.09 MPa, and a space velocity of 3 $Lg^{-1}{}_{cat}h^{-1}$. As a result, the conversion of isopentane measured at 1 hour after the beginning of the reaction is 42% and the selectivity to isopentene is 74.2%, while the conversion of isopentane measured at 3 hour after the beginning of the reaction is 33% and the selectivity to isopentene is 74.8%.

Example 37

33.3 g copper(II) nitrate, 3.3 g ammonium meta-vanadate and 26.0 g oxalic acid were dissolved in 1100 ml water, to obtain a mixture solution, and then into said solution, 211.2 g CMK-3, a mesoporous carbon having a specific surface area of 1320 $m^2 g^{-1}$ and a most probable pore size of 4.3 nm, was introduced. Then, the mixture was stirred for 10 min in a thermostatic water bath at 70° C., dried at 80° C., calcined at 650° C. under a nitrogen gas atmosphere for 5 hours, to obtained a mesoporous carbon supported copper based catalyst, which has a measured CuO amount by weight of 6.0% and a measured $V_2O_5$ amount by weight of 1.0%. The catalyst was loaded into a fixed-bed reactor, and to said reactor, a mixture feed, preheated to 340° C., of isopentane and $CO_2$ with a ratio by molar of isopentane to $CO_2$ is 1:6 was supplied, to react under the following reaction conditions: a reaction temperature of 560° C., a reaction pressure of 0.09 MPa, and a space velocity of 1 $Lg^{-1}{}_{cat}h^{-1}$. As a result, the conversion of isopentane measured at 1 hour after the beginning of the reaction is 49% and the selectivity to isopentene and isopentadiene in total is 80.6%, while the conversion of isopentane measured at 3 hour after the beginning of the reaction is 43% and the selectivity to isopentene and isopentadiene in total is 81.2%.

Example 38

33.3 g copper(II) nitrate, 3.3 g ammonium meta-vanadate, 6.0 g $LiNO_3$ and 26.0 g oxalic acid were dissolved in 1100 ml water, to obtain a mixture solution, and then into said solution, 211.2 g CMK-3, a mesoporous carbon having a specific surface area of 1320 $m^2 g^{-1}$ and a most probable pore size of 4.3 nm, was introduced. Then, the mixture was stirred for 10 min in a thermostatic water bath at 70° C., dried at 80° C., calcined at 650° C. under a nitrogen gas atmosphere for 5 hours, to obtained a mesoporous carbon supported copper based catalyst, which has a measured CuO amount by weight of 6.0%, a measured $V_2O_5$ amount by weight of 1.0%, and a measured $Li_2O$ amount by weight of 0.5%. The catalyst was loaded into a fixed-bed reactor, and to said reactor, a mixture feed, preheated to 330° C., of isopentane and $CO_2$ with a ratio by molar of isopentane to $CO_2$ is 1:11 was supplied, to react under the following reaction conditions: a reaction temperature of 560° C., a reaction pressure of 0.1 MPa, and a space velocity of 1 $Lg^{-1}{}_{cat}h^{-1}$. As a result, the conversion of isopentane measured at 1 hour after the beginning of the reaction is 51% and the selectivity to isopentene and isopentadiene in total is 83.6%, while the conversion of isopentane measured at 3 hour after the beginning of the reaction is 49% and the selectivity to isopentene and isopentadiene in total is 84.2%.

Example 39

The catalyst produced in Example 27 was loaded into a fixed-bed reactor, and to said reactor, a mixture feed, preheated to 330° C., of isopentane and $CO_2$ with a ratio by molar of isopentane to $CO_2$ is 1:8 was supplied, to react under the following reaction conditions: a reaction temperature of 550° C., a reaction pressure of 0.1 MPa, and a space velocity of 1 $Lg^{-1}{}_{cat}h^{-1}$. As a result, the conversion of isopentane measured at 1 hour after the beginning of the reaction is 48% and the selectivity to isopentene and isopentadiene in total is 80.2%, while the conversion of isopentane measured at 3 hour after the beginning of the reaction is 46% and the selectivity to isopentene and isopentadiene in total is 80.6%.

Example 40

35.1 g copper(II) chloride and 34.7 g ethylene glycol were dissolved in 1000 ml water, to obtain a mixture solution, and then into said solution, 210.2 g disordered mesoporous carbon having a specific surface area of 1230 $m^2 g^{-1}$ and a most probable pore size of 6.0 nm (produced according to Journal of Materials Chemistry, Vol. 19, 2009, pp. 7759-7764) was introduced. Then, the mixture was stirred for 10 min in a thermostatic water bath at 70° C., dried at 140° C., calcined at 640° C. under a nitrogen gas atmosphere for 5 hours, to obtained a mesoporous carbon supported copper based catalyst, which has a measured CuO amount by weight of 8.9%. The catalyst was loaded into a fixed-bed reactor, and to said reactor, a mixture feed, preheated to 350° C., of ethyl benzene and $CO_2$ with a ratio by molar of ethyl benzene to $CO_2$ is 1:8 was supplied, to react under the following reaction conditions: a reaction temperature of 490° C., a reaction pressure of 0.08 MPa, and a space velocity of 3 $Lg^{-1}_{cat}h^{-1}$. As a result, the conversion of ethyl benzene measured at 1 hour after the beginning of the reaction is 58% and the selectivity to styrene is 94.1%, while the conversion of ethyl benzene measured at 3 hour after the beginning of the reaction is 50% and the selectivity to styrene is 94.9%.

Example 41

35.1 g copper(II) chloride, 6.4 g $Zn(NO_3)_2$, and 45.6 g citric acid were dissolved in 1200 ml water, to obtain a mixture solution, and then into said solution, 210.2 g disordered mesoporous carbon having a specific surface area of 1230 $m^2$ $g^{-1}$ and a most probable pore size of 6.0 nm (produced according to Journal of Materials Chemistry, Vol. 19, 2009, pp. 7759-7764) was introduced. Then, the mixture was stirred for 10 min in a thermostatic water bath at 70° C., dried at 100° C., calcined at 640° C. under a nitrogen gas atmosphere for 5 hours, to obtained a mesoporous carbon supported copper based catalyst, which has a measured CuO amount by weight of 8.7% and a measured ZnO amount by weight of 1.0%. The catalyst was loaded into a fixed-bed reactor, and to said reactor, a mixture feed, preheated to 350° C., of ethyl benzene and $CO_2$ with a ratio by molar of ethyl benzene to $CO_2$ is 1:4 was supplied, to react under the following reaction conditions: a reaction temperature of 500° C., a reaction pressure of 0.09 MPa, and a space velocity of 6 $Lg^{-1}_{cat}h^{-1}$. As a result, the conversion of ethyl benzene measured at 1 hour after the beginning of the reaction is 58% and the selectivity to styrene is 93.9%, while the conversion of ethyl benzene measured at 3 hour after the beginning of the reaction is 53% and the selectivity to styrene is 94.4%.

Example 42

40.3 g copper(II) chloride, 5.1 g $Zn(NO_3)_2$, 3.8 g $KNO_3$ and 45.6 g citric acid were dissolved in 1200 ml water, to obtain a mixture solution, and then into said solution, 230.3 g disordered mesoporous carbon having a specific surface area of 1230 $m^2$ $g^{-1}$ and a most probable pore size of 6.0 nm (produced according to Journal of Materials Chemistry, Vol. 19, 2009, pp. 7759-7764) was introduced. Then, the mixture was stirred for 10 min in a thermostatic water bath at 70° C., dried at 160° C., calcined at 660° C. under a nitrogen gas atmosphere for 6 hours, to obtained a mesoporous carbon supported copper based catalyst, which has a measured CuO amount by weight of 9.1%, a measured ZnO amount by weight of 0.8% and a measured $K_2O$ amount by weight of 0.6%. The catalyst was loaded into a fixed-bed reactor, and to said reactor, a mixture feed, preheated to 350° C., of ethyl benzene and $CO_2$ with a ratio by molar of ethyl benzene to $CO_2$ is 1:8 was supplied, to react under the following reaction conditions: a reaction temperature of 470° C., a reaction pressure of 0.08 MPa, and a space velocity of 3 $Lg^{-1}_{cat}h^{-1}$. As a result, the conversion of ethyl benzene measured at 1 hour after the beginning of the reaction is 47% and the selectivity to styrene is 96.1%, while the conversion of ethyl benzene measured at 3 hour after the beginning of the reaction is 44% and the selectivity to styrene is 96.8%.

Example 43

18.9 g copper(II) nitrate, 1.8 g $SnCl_2$, 2.4 g $LiNO_3$, 2.7 g $KNO_3$ and 20.1 g ethylene glycol were dissolved in 2000 ml water, to obtain a mixture solution, and then into said solution, 148.8 g CMK-3, a mesoporous carbon having a specific surface area of 1320 $m^2$ $g^{-1}$ and a most probable pore size of 4.3 nm, was introduced. Then, the mixture was stirred for 10 min in a thermostatic water bath at 70° C., dried at 120° C., calcined at 590° C. under a nitrogen gas atmosphere for 3 hours, to obtained a mesoporous carbon supported copper based catalyst, which has a measured CuO amount by weight of 4.5%, a measured $SnO_2$ amount by weight of 0.9%, a measured $Li_2O$ amount by weight of 0.3% and a measured $K_2O$ amount by weight of 0.7%. The catalyst was loaded into a fixed-bed reactor, and to said reactor, a mixture feed, preheated to 350° C., of ethyl benzene and $CO_2$ with a ratio by molar of ethyl benzene to $CO_2$ is 1:4 was supplied, to react under the following reaction conditions: a reaction temperature of 480° C., a reaction pressure of 0.1 MPa, and a space velocity of 2 $Lg^{-1}_{cat}h^{-1}$. As a result, the conversion of ethyl benzene measured at 1 hour after the beginning of the reaction is 62% and the selectivity to styrene is 96.4%, while the conversion of ethyl benzene measured at 3 hour after the beginning of the reaction is 59% and the selectivity to styrene is 96.9%.

Example 44

33.0 g copper(II) acetate and 34.7 g citric acid were dissolved in 1000 ml water, to obtain a mixture solution, and then into said solution, 190.3 g disordered mesoporous carbon having a specific surface area of 1230 $m^2$ $g^{-1}$ and a most probable pore size of 6.0 nm (produced according to Journal of Materials Chemistry, Vol. 19, 2009, pp. 7759-7764) was introduced. Then, the mixture was stirred for 10 min in a thermostatic water bath at 70° C., dried at 140° C., calcined at 620° C. under a nitrogen gas atmosphere for 8 hours, to obtained a mesoporous carbon supported copper based catalyst, which has a measured CuO amount by weight of 6.9%. The catalyst was loaded into a moving bed reactor, and to said reactor, a mixture feed, preheated to 340° C., of ethyl cyclohexane and $CO_2$ with a ratio by molar of ethyl cyclohexane to $CO_2$ is 1:5 was supplied, to react under the following reaction conditions: a reaction temperature of 600° C., a reaction pressure of 0.08 MPa, and a space velocity of 2 $Lg^{-1}_{cat}h^{-1}$. As a result, the conversion of ethyl cyclohexane measured at 1 hour after the beginning of the reaction is 56% and the selectivity to vinyl cyclohexane and ethyl cyclohexene in total is 72.2%, while the conversion of ethyl cyclohexane measured at 3 hour after the beginning of the reaction is 47% and the selectivity to vinyl cyclohexane and ethyl cyclohexene in total is 73.2%.

Example 45

34.0 g copper(II) acetate, 6.1 g $Al(NO_3)_3$ and 39.2 g citric acid were dissolved in 1200 ml water, to obtain a mixture solution, and then into said solution, 230.1 g CMK-3, a mesoporous carbon having a specific surface area of 1320 $m^2$ $g^{-1}$ and a most probable pore size of 4.3 nm, was introduced. Then, the mixture was stirred for 10 min in a thermostatic water bath at 70° C., dried at 100° C., calcined at 630° C. under a nitrogen gas atmosphere for 6 hours, to obtained a mesoporous carbon supported copper based catalyst, which has a measured CuO amount by weight of 5.8% and a measured $Al_2O_3$ amount by weight of 0.7%. The catalyst was loaded into a fixed-bed reactor, and to said reactor, a mixture feed, preheated to 330° C., of ethyl cyclohexane and $CO_2$ with a ratio by molar of ethyl cyclohexane to $CO_2$ is 1:10 was supplied, to react under the following reaction conditions: a reaction temperature of 620° C., a reaction pressure of 0.1 MPa, and a space velocity of 3 $Lg^{-1}_{cat}h^{-1}$. As a result, the conversion of ethyl cyclohexane measured at 1 hour after the beginning of the reaction is 58% and the selectivity to vinyl cyclohexane and ethyl cyclohexene in total is 76.3%, while the conversion of ethyl cyclohexane measured at 3 hour after the beginning of the reaction is 49% and the selectivity to vinyl cyclohexane and ethyl cyclohexene in total is 76.8%.

Example 46

43.3 g copper(II) acetate, 2.8 g ammonium meta-vanadate, 6.0 g cerium(III) nitrate and 34.0 g oxalic acid were dissolved in 1100 ml water, to obtain a mixture solution, and then into said solution, 211.2 g CMK-3, a mesoporous carbon having a specific surface area of 1320 $m^2 g^{-1}$ and a most probable pore size of 4.3 nm, was introduced. Then, the mixture was stirred for 10 min in a thermostatic water bath at 70° C., dried at 80° C., calcined at 650° C. under a nitrogen gas atmosphere for 5 hours, to obtained a mesoporous carbon supported copper based catalyst, which has a measured CuO amount by weight of 7.6%, a measured $V_2O_5$ amount by weight of 0.8% and a measured $CeO_2$ amount by weight of 1.1%. The catalyst was loaded into a fixed-bed reactor, and to said reactor, a mixture feed, preheated to 350° C., of ethyl cyclohexane and $CO_2$ with a ratio by molar of ethyl cyclohexane to $CO_2$ is 1:11 was supplied, to react under the following reaction conditions: a reaction temperature of 600° C., a reaction pressure of 0.1 MPa, and a space velocity of 8 $Lg^{-1}_{cat}h^{-1}$. As a result, the conversion of ethyl cyclohexane measured at 1 hour after the beginning of the reaction is 57% and the selectivity to vinyl cyclohexane and ethyl cyclohexene in total is 76.2%, while the conversion of ethyl cyclohexane measured at 3 hour after the beginning of the reaction is 51% and the selectivity to vinyl cyclohexane and ethyl cyclohexene in total is 77.5%.

Example 47

The catalyst produced in Example 27 was loaded into a fixed-bed reactor, and to said reactor, a mixture feed, preheated to 330° C., of ethyl cyclohexane and $CO_2$ with a ratio by molar of ethyl cyclohexane to $CO_2$ is 1:8 was supplied, to react under the following reaction conditions: a reaction temperature of 600° C., a reaction pressure of 0.1 MPa, and a space velocity of 1 $Lg^{-1}_{cat}h^{-1}$. As a result, the conversion of ethyl cyclohexane measured at 1 hour after the beginning of the reaction is 67% and the selectivity to vinyl cyclohexane and ethyl cyclohexene in total is 80.2%, while the conversion of ethyl cyclohexane measured at 3 hour after the beginning of the reaction is 65% and the selectivity to vinyl cyclohexane and ethyl cyclohexene in total is 80.8%.

What is claimed is:

1. A mesoporous carbon supported copper based catalyst, comprising mesoporous carbon, a copper component and an auxiliary element supported on said mesoporous carbon,
   wherein, the auxiliary element (expressed as oxide) is one or more selected from $V_2O_5$, $Li_2O$, MgO, CaO, $Ga_2O_3$, ZnO, $Al_2O_3$, $CeO_2$, $La_2O_3$, $SnO_2$ and $K_2O$,
   the copper component (calculated as CuO) is present in an amount ranging from 2 wt % to 20 wt % based on the total weight of the catalyst,
   the auxiliary element (calculated as the aforesaid oxide) is present in an amount ranging from 0 wt % to 3 wt % based on the total weight of the catalyst, and
   the mesoporous carbon is present in an amount ranging from 77.1 wt % to 98 wt % on the total weight of the catalyst, and
   further wherein the mesoporous carbon has a BET specific surface area ranging from 900 $m^2 g^{-1}$-3100 $m^2 g^{-1}$, a most probable pore size ranging from 2 nm to 8 nm, a pore volume ranging from 0.4 $mlg^{-1}$ to 3.2 $mlg^{-1}$, and a mesoporosity ranging from 50% to 100%.

2. The mesoporous carbon supported copper based catalyst according to claim 1, wherein the catalyst is substantially consisted of the mesoporous carbon, the copper component and the auxiliary element.

3. The mesoporous carbon supported copper based catalyst according to claim 1, wherein the mesoporous carbon has a BET specific surface area ranging from 1200 $m^2 g^{-1}$ to 3100 $m^2 g^{-1}$, a pore volume ranging from 1.0 $mlg^{-1}$ to 2.1 $mlg^{-1}$, a mesoporosity ranging from 75% to 100%.

4. The mesoporous carbon supported copper based catalyst according to claim 1, wherein the mesoporous carbon is one or more selected from a mesoporous carbon having an ordered pore structure, a carbon nano-tube, a carbon nano-rod, and a mesoporous carbon having a disordered pore structure.

5. A process for converting $C_2$ to $C_{12}$ chain alkyl group into its corresponding chain alkenyl group comprising:
   contacting a $C_2$ to $C_{12}$ chain alkyl group with the mesoporous carbon supported copper based catalyst according to claim 1.

6. The process according to claim 5, wherein the $C_2$ to $C_{12}$ chain alkyl compound is isobutane and the corresponding chain alkenyl group is isobutene, and the process comprises contacting the mesoporous carbon supported copper based catalyst with a mixture feed comprising isobutane and $CO_2$, to convert isobutane into isobutene by a catalytic dehydrogenation reaction.

7. The process according to claim 6, wherein the catalytic dehydrogenation reaction conditions comprise: a reaction temperature ranging from 550° C. to 650° C., a reaction pressure ranging from 0.05 MPa to 1.0 MPa, a space velocity of ranging from 0.5 $Lg^{-1}_{cat} h^{-1}$ to 8 $Lg^{-1}_{cat} h^{-1}$, and ratio by molar of isobutane to $CO_2$ ranging from 1:0.5 to 1:11.

8. The mesoporous carbon supported copper based catalyst according to claim 1, wherein the auxiliary element (expressed as oxide) is $SnO_2$, $Li_2O$, a combination of $SnO_2$ and $Li_2O$, a combination of $SnO_2$ and $K_2O$, a combination of $Li_2O$ and $K_2O$, or a combination of $SnO_2$, $K_2O$ and $Li_2O$.

9. The mesoporous carbon supported copper based catalyst according to claim 1, wherein:
   the auxiliary element (calculated as the aforesaid oxide) is present in an amount ranging from 0% to 2.9 wt % based on the total weight of the catalyst, and
   the mesoporous carbon is present in an amount ranging from 83 wt to 96.8 wt % based on the total weight of the catalyst.

10. The mesoporous carbon supported copper based catalyst according to claim 1, wherein:
    the copper component (calculated as CuO) is present in an amount ranging from 3 wt % to 15 wt % based on the total weight of the catalyst,
    the auxiliary element (calculated as the aforesaid oxide) is present in an amount ranging from 0.2 wt % to 2.0 wt % based on the total weight of the catalyst, and
    the remaining wt % of the catalyst is the mesoporous carbon.

11. A process for producing a mesoporous carbon supported copper based catalyst comprising:
    (1) contacting a copper component precursor with an auxiliary element precursor and a mesoporous carbon to obtain an intermediate product, and (2) calcining the intermediate product to obtain the mesoporous carbon supported copper based catalyst, wherein, the auxiliary element (expressed as oxide) is one or more selected from $V_2O_5$, $Li_2O$, MgO, CaO, $Ga_2O_3$, ZnO, $Al_2O_3$, $CeO_2$, $La_2O_3$, $SnO_2$ and $K_2O$, wherein in the mesoporous carbon supported copper based catalyst resulted from the calcination;

the copper component (calculated as CuO) is present in an amount ranging from 2 wt % to 20 wt % based on the total weight of the catalyst, the auxiliary element (calculated as the aforesaid oxide) i ent in an amount an from 0 wt % to 3 wt % based on the total weight of the catalyst, and the mesoporous carbon is present in an amount ranging from 77.1 wt % to 98 wt % based on the total weight of the catalyst further wherein the mesoporous carbon has a BET specific surface area ranging from 900 $m^2$ $g^{-1}$-3100 $m^2$ $g^{-1}$, a most probable pore size ranging from 2 nm to 8 nm, a pore volume ranging from 0.4 $mlg^{-1}$ to 3.2 $mlg^{-1}$, and a mesoporosity ranging from 50% to 100%.

12. The process according to claim 11, wherein the contacting is conducted in the presence of a metal complexing agent, and the ratio by weight of the metal complexing agent to the copper component precursor is in the range of from 0.4 to 2.0.

13. The process according to claim 11, wherein the calcination is conducted under a substantially oxygen free inert gas atmosphere at 500 to 750® C.

14. The process according to claim 11, wherein the auxiliary element (expressed as oxide) is $SnO_2$, $Li_2O$, a combination of $SnO_2$ and $Li_2O$, a combination of $SnO_2$ and $K_2O$, a combination of $Li_2O$ and $K_2O$, or a combination of $SnO_2$, $K_2O$ and $Li_2O$.

15. The process according to claim 11, wherein:

the auxiliary element (calculated as the aforesaid oxide) is present in an amount ranging from 0% to 2.9 wt % based on the total weight of the catalyst, and the mesoporous carbon is present in an amount ranging from 83 wt to 96.8 wt % based on the total weight of the catalyst.

16. The process according to claim 11, wherein:

the copper component (calculated as CuO) is present in an amount ranging from 3 wt % to 15 wt % based on the total weight of the catalyst, the auxiliary element (calculated as the aforesaid oxide) is present in an amount ranging from 0.2 wt % to 2.0 wt % based on the total weight of the catalyst, and the remaining wt % of the catalyst is the mesoporous carbon.

17. The process according to claim 11, wherein the mesoporous carbon has a BET specific surface area ranging from 1200 $m^2$ $g^{-1}$ to 3100 $m^2$ $g^{-1}$, a pore volume ranging from 1.0 $mlg^{-1}$ to 2.1 $mlg^{-1}$, a mesoporosity ranging from 75% to 100%.

* * * * *

UNITED STATES PATENT AND TRADEMARK OFFICE
CERTIFICATE OF CORRECTION

PATENT NO. : 8,785,343 B2  Page 1 of 1
APPLICATION NO. : 13/595260
DATED : July 22, 2014
INVENTOR(S) : Jingwei Liu et al.

It is certified that error appears in the above-identified patent and that said Letters Patent is hereby corrected as shown below:

In the Claims

Claim 11, Col. 31, Lines 11-12, "I ent" should read as --is present--.

Claim 11, Col. 31, Line 12, "amount an" should read as --amount ranging--.

Claim 13, Col. 31, Line 29, "750® C" should read as --750°C--.

Signed and Sealed this
Twenty-eighth Day of October, 2014

Michelle K. Lee
*Deputy Director of the United States Patent and Trademark Office*